United States Patent [19]
Urdahl et al.

[11] Patent Number: 5,658,240
[45] Date of Patent: Aug. 19, 1997

[54] BLOOD COMPONENT COLLECTION SYSTEM WITH OPTIMIZER

[75] Inventors: Steven Gage Urdahl, Golden; Timothy Michael Gordon, Littleton; Thomas James Minyard, Golden, all of Colo.; Emery Joseph Stephans, Stamford, Conn.

[73] Assignee: Cobe Laboratories, Inc., Arvada, Colo.

[21] Appl. No.: 327,521

[22] Filed: Oct. 21, 1994

Related U.S. Application Data

[63] Continuation-in-part of Ser. No. 140,254, Oct. 21, 1993, which is a continuation-in-part of Ser. No. 912,973, Jul. 10, 1992, abandoned, Ser. No. 845,877, Mar. 4, 1992, abandoned, and Ser. No. 110,432, Aug. 23, 1993, Pat. No. 5,437,624.

[51] Int. Cl.$^6$ .................................................. A61M 37/00
[52] U.S. Cl. ........................................ 604/5; 604/4
[58] Field of Search .................. 364/413.01, 413.07; 128/DIG. 13; 604/4–6, 29

[56] References Cited

U.S. PATENT DOCUMENTS

| | | | |
|---|---|---|---|
| 4,457,750 | 7/1984 | Hill | 604/65 |
| 4,657,529 | 4/1987 | Prince et al. | 604/6 |
| 4,810,090 | 3/1989 | Boucher et al. | 356/39 |
| 4,851,126 | 7/1989 | Schoendorfer | 210/651 |
| 4,968,295 | 11/1990 | Neumann | 604/6 |
| 5,024,231 | 6/1991 | Fledschum et al. | 128/654 |
| 5,178,603 | 1/1993 | Prince | 604/6 |
| 5,324,422 | 6/1994 | Colleran et al. | 210/85 |

FOREIGN PATENT DOCUMENTS

| | | |
|---|---|---|
| 0 580 299 A1 | 1/1994 | European Pat. Off. . |
| WO 84/00112 | 1/1984 | WIPO . |

OTHER PUBLICATIONS

COBE Spectra™ Operator's Manual, Section 1—Introduction.

*Primary Examiner*—Randall L. Green
*Assistant Examiner*—Rob Clarke
*Attorney, Agent, or Firm*—Sheridan Ross & McIntosh

[57] ABSTRACT

A blood component collection system with optimization capabilities. In one embodiment, the blood component collection system includes a central input station (e.g., computer) and a plurality of blood component collection assemblies. These blood component collection assemblies include a blood component collection device and an operator interface module (e.g., computer). Various types of data are maintained on the collection procedures performed in the blood component collection system and are utilized to generate various types of reports for optimizing system operations.

28 Claims, 42 Drawing Sheets

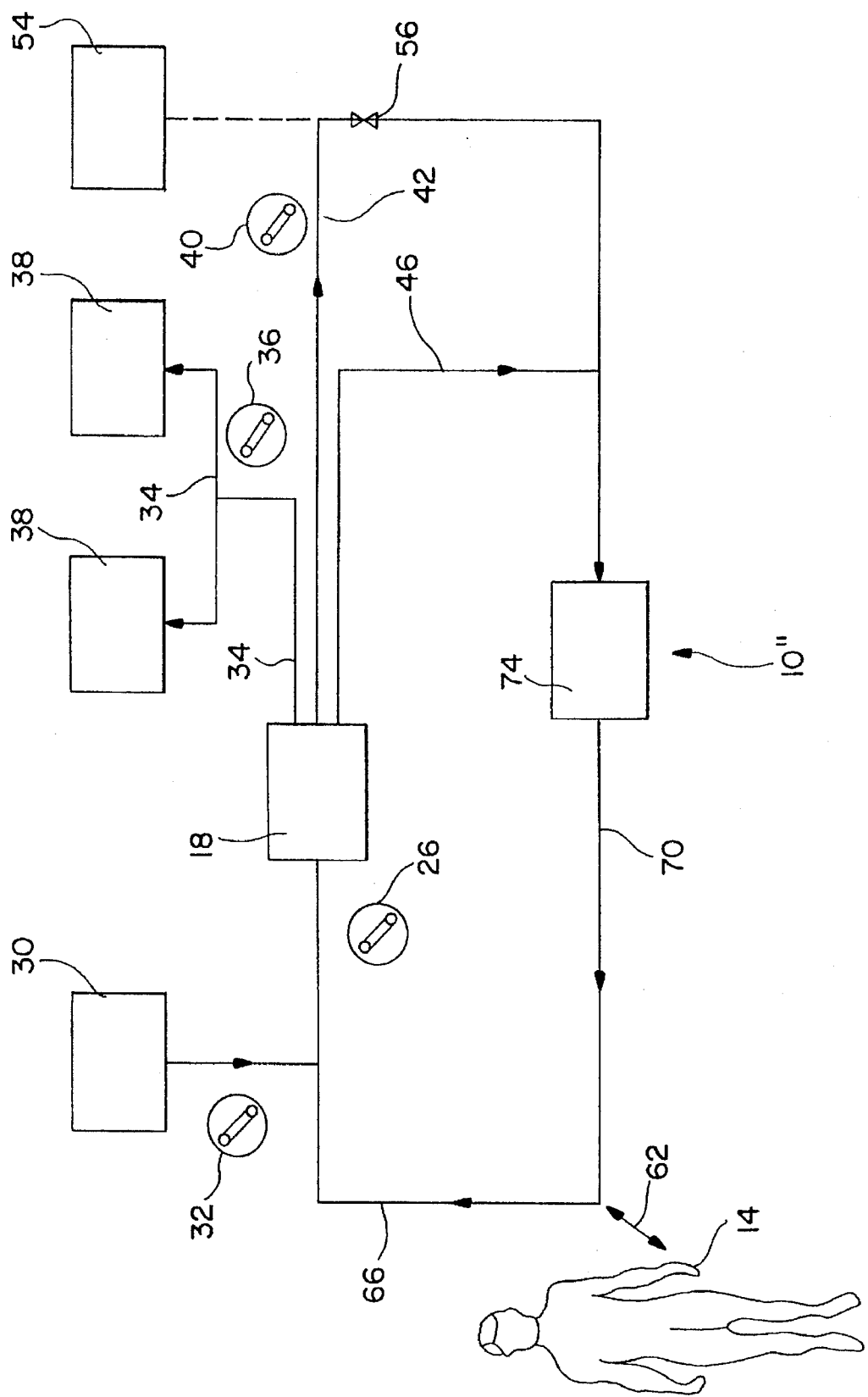

APOLLOnet - Automated Data Management System

DONOR/PATIENT FILE REPORT

COBE BCT
1201 OAK ST.

Page 1
10/19/94
12:14:58

Name: BERRA, YOGI      ID Number: 7290-5600
Social Security Number: 123-45-6789      Birth Date (mm/dd/yy): 11/04/26

Procedures included in this report: last procedure only
================================================================================
- - DONOR/PATIENT DEMOGRAPHICS - -

```
                    Address:    *  645 CATCHER'S LANE
                                *  ?
                City & State:   *  NEW YORK              , * NY
                Zip & Country:  *  08679         * USA Phone (Home):   *  (213) 222-3333  /4444.
                Phone (Work):   *  (213) 666-7777  /8888
```

Donor/Patient Chart:

. . . . . . . . . . . . . . . . . . . . . . . . . . . . . . . . . . . . . . . .
- - BLOOD & PLATELET TYPINGS - -

```
        Blood Type:    *  A+                  HLA A:   *  10
                                                       *  10
               CMV:    *  +                   HLA B:   *  13
                                                       *  13
    IgA Deficiency?:   *  Y                   HLA C:   *  W10 (W3)
                                                       *  W10 (W3)
                                              HLA D:   *  W10
             PLA-1:    *  +                            *  W10
                                              HLA DR:  *  2
             HpA1:     *  +                            *  2
             HpA2:     *  +                   HLA DQ:  *  W2
             HpA3:     *  +                            *  W2
             HpA4:     *  +                   HLA DP:  *  W2
             HpA5:     *  +                            *  W2

Race:    *  AFRICAN AMERICAN
```

FIG. 9B

DONOR/PATIENT FILE REPORT  Page 2
 10/19/94
Name: BERRA, YOGI   ID Number: 7290-5600  12:14:58
Social Security Number: 123-45-6789   Birth Date (mm/dd/yy): 11/04/26

– – DISEASE & VIRAL SCREENINGS – –

```
            HIV 1/2:   *   +

HBsAg:     *   +
          Anti-HBc:    *   +

Anti-HCV:    *   +

HTLV I:    *   +

RPR:     *   +

ALT (IU/dl):  *   17.0
      ALT Acceptable?: *   N
```

Note: This information is confidential.

– – CONTACTS – –

```
    Emergency Contact:  *  NN
      Emergency Phone:  *  OO

Doctor's Name:  *  PP
       Doctor's Phone:  *  QQ

Hospital:  *  KAISER
     Hospital ID Number: * SS

Employer:  *  TT
                  Job:  *  UU
```

FIG. 9C

DONOR/PATIENT FILE REPORT

Page 3
10/19/94
12:14:58

Name: BERRA, YOGI     ID Number: 7290-5600
Social Security Number: 123-45-6789     Birth Date (mm/dd/yy): 11/04/26

Run Date: 09/07/94    Time: 14:38:34
Unit/Run Numbers: 1212121212
Operator ID: DEL      Machine ID:   0

====================================================================

-- HEMATOLOGY --

| - PREPROCEDURE - | | | - POSTPROCEDURE - | |
|---|---|---|---|---|
| RBC Count | (E6/ul): | 4.2 | | |
| HGB | (g/dl): | 14.0 | | |
| Hct | (%): | 55 | Hct : | 43 |
| PLT Count | (E3/ul): | 1234 | PLT Count : | 299 |
| WBC Count | (/ul): | 7.0 | | |
| Neutrophils: Seg/Gran | (%): | 41.0 | | |
| Neutrophils: Bands | (%): | 42.0 | | |
| Eosinophils | (%): | 43.0 | | |
| Basophils | (%): | 44.0 | | |
| Lymphocytes | (%): | 45.0 | | |
| Monocytes | (%): | 46.0 | | |
| MCH | (pg): | 28.0 | | |
| MCHC | (%): | 32.0 | | |
| MCV | (%): | 89.0 | | |
| RDW | (units): | 47.0 | | |
| MPV | (ul): | 48.0 | | |

.......................................................

-- BLOOD CHEMISTRY --

| | | |
|---|---|---|
| IgG | (mg/dl): | 1100.0 |
| IgM | (mg/dl): | 99.0 |
| IgA | (mg/dl): | 299.0 |
| Total Protein | (g/dl): | 6.0 |
| Albumin | (g/dl): | 59.0 |
| Globulin | (g/dl): | 49.0 |
| Glucose | (mg/dl): | 87.0 |
| Cholesterol | (mg/dl): | 221.0 |
| Triglycerides | (mg/dl): | 99.0 |

FIG. 9D

DONOR/PATIENT FILE REPORT

Page 4
10/19/94
12:14:58

Name: BERRA, YOGI   ID Number: 7290-5600
Social Security Number: 123-45-6789   Birth Date (mm/dd/yy): 11/04/26

Run Date: 09/07/94   Time: 14:38:34
Unit/Run Numbers: 1212121212
Operator ID: DEL   Machine ID:   0

========================================================================

-- PROCEDURE (DONOR/PATIENT) --

| | |
|---:|:---|
| Procedure: | PLATELET |
| Dual Needle?: | Y |
| Collect Plasma?: | Y |
| Access Needle: | 18 |
| Return Needle: | 18 |
| Access Site: | LEFT FEMORAL |
| Return Site: | RIGHT FEMORAL |
| Allergy: | POLLEN |
| Target Run Time (min): | 119 |
| Data Recording Interval (min): | 6 |
| Inlet/AC Ratio Method: | L |
| Inlet/AC Ratio   : | 7.4 |

- MAXIMUM FLOW RATES -

| | |
|---:|:---|
| SN Inlet (ml/min): | 45.0 |
| DN Inlet (ml/min): | 49.0 |
| AC Infusion (ml/min/1BV): | 1.1 |

. . . . . . . . . . . . . . . . . . . . . . . . . . . . . . . . . . . . . . . . . . . . . . . . . .

-- THERAPEUTICS --

| | |
|---:|:---|
| Disease: | MULTIPLE SCLEROSIS |
| Bleeding Time (min): | 3.0 |
| Respiration (l/min): | 14 |
| Plasma Volume (ml): | 2758 |
| Replacement Volume (ml): | 221 |
| Fluid Balance (%): | 110.0 |

- RED BLOOD CELL EXCHANGE -

| | |
|---:|:---|
| Avg. Replacement Hct (%): | 87 |
| End Hct (%): | 69 |
| FCR (%): | 43 |

FIG. 9E

DONOR/PATIENT FILE REPORT                                                                 Page  5
                                                                                          10/19/94
Name: BERRA, YOGI          ID Number: 7290-5600                                           12:14:58
Social Security Number: 123-45-6789       Birth Date (mm/dd/yy): 11/04/26

Run Date: 09/07/94    Time: 14:38:34
Unit/Run Numbers: 1212121212
Operator ID: DEL                              Machine ID:     0
================================================================================
                            - - PROCEDURE END - -

Procedure:    PLATELET
                                Dual Needle?:   Y

Start Time:   ??:??
                                   Stop Time:   14:38

- - VITALS - -
                        Blood Pressure (mmHg):  110/ 70
                              Temperature (F):  98.5
                                 Pulse (/min):  65
                                  Height (ft):  5'  11"
                                  Weight (lb):  188
                       Total Blood Volume (ml): 5091
                                Blood Type:  *  A+
                                       CMV:  *  +
                                       Sex:  *  M

- - HEMATOLOGY - -
                        RBC Count   (E6/ul):    4.2
                        HGB         (g/dl):     14.0
                        Hct         (%):        55
                        PLT Count   (E3/ul):    1234
                        WBC Count   (/ul):      7.0
. . . . . . . . . . . . . . . . . . . . . . . . . . . . . . . . . . . . . . . .
                           - - RUN RESULTS (PLATELET) - -

PLT Yield  (E11):    2.0
                              CCM Yield  (E11):    4.9
                        PLT Collect Conc. (E3/ul): 0

PLT Volume    (ml):  400
                        AC in PLT Volume    (ml):  800
                        Net PLT Volume      (ml):  -400

Plasma Volume (ml):  500
                        AC in Plasma Volume (ml):  100
                        Net Plasma Volume   (ml):  400

Inlet/AC Ratio Method:  L
                        AC Infusion Rate (ml/min/1BV):  1.1
                           Inlet Volume incl. AC (ml):  6000
                                      AC Volume (ml):  600

Run Time (min):  100.0

Disposables Used:

FIG. 9F

DONOR/PATIENT FILE REPORT

Page 6
10/19/94
12:14:58

Name: BERRA, YOGI        ID Number: 7290-5600
Social Security Number: 123-45-6789        Birth Date (mm/dd/yy): 11/04/26

Run Date: 09/07/94    Time: 14:38:34
Unit/Run Numbers: 1212121212
Operator ID: DEL                    Machine ID:    0
------------------------------------------------------------------------

No Entries.

Procedure Notes:

FIG. 9G

DONOR/PATIENT FILE REPORT

Page 7
10/19/94
12:14:58

Name: BERRA, YOGI  ID Number: 7290-5600
Social Security Number: 123-45-6789  Birth Date (mm/dd/yy): 11/04/26

Run Date: 09/07/94  Time: 14:38:34
Unit/Run Numbers: 1212121212
Operator ID: DEL  Machine ID: 0

| TIME | AC FLOW | AC VOL | INLET FLOW | INLET VOL | PLASMA FLOW | PLASMA VOL | COLLECT FLOW | COLLECT VOL | AC RATIO | YIELD PLT PR |
|---|---|---|---|---|---|---|---|---|---|---|
| 14:28:55 | NOTE: | --- Start of data logging | | | | | | | | |
| 14:37:33 | 10.0 | 0 | 50.0 | 0 | 20.0 | 0 | 30.0 | 0 | 0.0 | 0.00 |
| 14:37:45 | 10.0 | 120 | 51.0 | 1200 | 20.0 | 100 | 30.0 | 80 | 1.5 | 4.67 |
| 14:37:50 | ALARM: | FAILURE # 1: Display Processor – ___ | | | | | | | | |
|  |  | Record #. CONTINUE to retry or Rinse. * | | | | | | | | |
| 14:37:50 | 10.0 | 180 | 51.0 | 1800 | 20.0 | 150 | 30.0 | 120 | 2.2 | 4.33 |
| 14:37:56 | 10.0 | 240 | 52.0 | 2400 | 20.0 | 200 | 30.0 | 160 | 3.0 | 4.00 |
| 14:38:08 | 10.0 | 360 | 53.0 | 3600 | 20.0 | 300 | 30.0 | 240 | 4.4 | 3.33 |
| 14:37:50 | CLEARED: | FAILURE # 1: Display Processor – ___ | | | | | | | | |
|  |  | Record #. CONTINUE to retry or Rinse. * | | | | | | | | |
| 14:38:14 | 10.0 | 420 | 53.0 | 4200 | 20.0 | 350 | 30.0 | 280 | 5.2 | 3.00 |
| 14:38:20 | 10.0 | 480 | 54.0 | 4800 | 20.0 | 400 | 30.0 | 320 | 5.9 | 2.67 |
| 14:38:32 | NOTE: | --- End of Run detected | | | | | | | | |
| 14:38:32 | 10.0 | 600 | 55.0 | 6000 | 20.0 | 500 | 30.0 | 400 | 7.4 | 2.00 |
| 14:59:39 | NOTE: | --- Run data saved to diskette | | | | | | | | |

FIG. 10A

APOLLOnet – Automated Data Management System

DONOR/PATIENT VITALS REPORT

Page 1
10/19/94
12:16:24

COBE BCT
1201 OAK ST.

Name: BERRA, YOGI     ID Number: 7290-5600
Social Security Number: 123-45-6789     Birth Date (mm/dd/yy): 11/04/26

Procedures included in this report: last procedure only
=====================================================================

– – BLOOD & PLATELET TYPINGS – –

| | | | | |
|---|---|---|---|---|
| Blood Type: | * A+ | | HLA A: | * 10 |
| | | | | * 10 |
| CMV: | * + | | HLA B: | * 13 |
| | | | | * 13 |
| IgA Deficiency?: | * Y | | HLA C: | * W10 (W3) |
| | | | | * W10 (W3) |
| | | | HLA D: | * W10 |
| PLA-1: | * + | | | * W10 |
| | | | HLA DR: | * 2 |
| HpA1: | * + | | | * 2 |
| HpA2: | * + | | HLA DQ: | * W2 |
| HpA3: | * + | | | * W2 |
| HpA4: | * + | | HLA DP: | * W2 |
| HpA5: | * + | | | * W2 |

Race:   * AFRICAN AMERICAN

– – DISEASE & VIRAL SCREENINGS – –

HIV 1/2:   * +

HBsAg:   * +
Anti-HBc:   * +

Anti-HCV:   * +

HTLV I:   * +

RPR:   * +

ALT (IU/dl):   * 17.0
ALT Acceptable?:   * N

Note: This information is confidential.

FIG. 10B

DONOR/PATIENT VITALS REPORT

Page . 2
10/19/94
12:16:24

Name: BERRA, YOGI    ID Number: 7290-5600
Social Security Number: 123-45-6789    Birth Date (mm/dd/yy): 11/04/26

Run Date: 09/07/94    Time: 14:38:34
Unit/Run Numbers: 1212121212
Operator ID: DEL    Machine ID:    0

\- - HEMATOLOGY - -

| | - PREPROCEDURE - | | | - POSTPROCEDURE - | |
|---|---|---|---|---|---|
| | RBC Count | (E6/ul): | 4.2 | | |
| | HGB | (g/dl): | 14.0 | | |
| | Hct | (%): | 55 | Hct    : | 43 |
| | PLT Count | (E3/ul): | 1234 | PLT Count : | 299 |
| | WBC Count | (/ul): | 7.0 | | |
| Neutrophils: | Seg/Gran | (%): | 41.0 | | |
| Neutrophils: | Bands | (%): | 42.0 | | |
| Eosinophils | | (%): | 43.0 | | |
| Basophils | | (%): | 44.0 | | |
| Lymphocytes | | (%): | 45.0 | | |
| Monocytes | | (%): | 46.0 | | |
| | MCH | (pg): | 28.0 | | |
| | MCHC | (%): | 32.0 | | |
| | MCV | (%): | 89.0 | | |
| | RDW | (units): | 47.0 | | |
| | MPV | (ul): | 48.0 | | |

\- - BLOOD CHEMISTRY - -

| | | |
|---|---|---|
| IgG | (mg/dl): | 1100.0 |
| IgM | (mg/dl): | 99.0 |
| IgA | (mg/dl): | 299.0 |
| Total Protein | (g/dl): | 6.0 |
| Albumin | (g/dl): | 59.0 |
| Globulin | (g/dl): | 49.0 |
| Glucose | (mg/dl): | 87.0 |
| Cholesterol | (mg/dl): | 221.0 |
| Triglycerides | (mg/dl): | 99.0 |

\- - VITALS - -

| | | |
|---|---|---|
| Blood Pressure | (mmHg): | 110/ 70 |
| Temperature | (F): | 98.5 |
| Pulse | (/min): | 65 |
| Height | (ft): | 5' 11" |
| Weight | (lb): | 188 |
| Total Blood Volume | (ml): | 5091 |

FIG. 11A

APOLLOnet – Automated Data Management System

PROCEDURE SUMMARY REPORT

Page 1
10/19/94
12:20:34

COBE BCT
1201 OAK ST.

Name: BERRA, YOGI     ID Number: 7290-5600
Social Security Number: 123-45-6789     Birth Date (mm/dd/yy): 11/04/26

Run Date: 09/07/94    Time: 13:48:23
Unit/Run Numbers: 1234567890
Operator ID: DEL                  Machine ID:   0

============================================================================

– – PROCEDURE END – –

Procedure:    PLATELET
      Dual Needle?:    Y

Start Time:    ??:??
          Stop Time:    13:48

– – VITALS – –

Blood Pressure (mmHg):   *   111/ 60
    Temperature (F):   *    98.6
        Pulse (/min):   *     66
          Height (ft):       5' 11"
         Weight (lb):       188
Total Blood Volume (ml):      5091
          Blood Type:   *     A+
                 CMV:   *     +
                  Sex:   *     M

– – HEMATOLOGY – –

RBC Count    (E6/ul):   *     5.0
   HGB            (g/dl):   *    15.0
   Hct              (%):       55
   PLT Count    (E3/ul):      1234
   WBC Count      (/ul):   *     8.0

FIG. 11B

PROCEDURE SUMMARY REPORT

Page 2
10/19/94
12:20:34

Name: BERRA, YOGI     ID Number: 7290-5600
Social Security Number: 123-45-6789     Birth Date (mm/dd/yy): 11/04/26

Run Date: 09/07/94   Time: 13:48:23
Unit/Run Numbers: 1234567890
Operator ID: DEL                 Machine ID:   0

-- RUN RESULTS (PLATELET) --

|  |  |
|---|---|
| PLT Yield (E11): | 2.0 |
| CCM Yield (E11): | 4.9 |
| PLT Collect Conc. (E3/ul): | 0 |
| PLT Volume (ml): | 400 |
| AC in PLT Volume (ml): | 800 |
| Net PLT Volume (ml): | -400 |
| Plasma Volume (ml): | 500 |
| AC in Plasma Volume (ml): | 100 |
| Net Plasma Volume (ml): | 400 |
| Inlet/AC Ratio Method: | L |
| AC Infusion Rate (ml/min/1BV): | 1.1 |
| Inlet Volume incl. AC (ml): | 6000 |
| AC Volume (ml): | 600 |
| Run Time (min): | 100.0 |

Disposables Used:
    No Entries.

Procedure Notes:

FIG. 12

```
APOLLOnet - Automated Data Management System                        Page    1
                                                                    10/19/94
DONOR PRODUCT REPORT                                                12:19:31

COBE BCT
1201 OAK ST.

Name:  BERRA, YOGI       ID Number:  7290-5600
Social Security Number:  123-45-6789         Birth Date (mm/dd/yy): 11/04/26

Procedures included in this report:  all procedures

Run Date: 09/07/94 Time:  13:48:23
Unit/Run Numbers:  1234567890
Operator ID: DEL                             Machine ID:    0
===============================================================================
                         - - PRODUCT/RECIPIENT - -

- PRODUCT -
                   Unit/Run Number:    1234567890
                Use Data in Run Totals?:       N
                       PLT Count (E11):      3.3
                       RBC Count   (%):      0.0
                       WBC Count  (E5):      0.0
            PLT Collect Conc. (E3/ul):     1444
                  Collect Volume (ml):      230
                   Plasma Volume (ml):      250
             Expiration Date (mm/dd/yy):    /  /
                   Ship Date (mm/dd/yy):    /  /

- RECIPIENT -
                       Name   (Last):
                            (First):
                          ID Number:
             Transfusion Date (mm/dd/yy):    /  /
                   PLT Precount (E3/ul):         0
                  PLT Postcount (E3/ul):         0
```

FIG. 13A

PROCEDURE MACHINE REPORT

Page 2
09/21/94
10:44:32

Name:     ANDREA          ID Number:  ?
Social Security Number:  445-66-8855     Birth Date (mm/dd/yy):  12/13/63

Run Date: 09/20/94   Time:  20:08:10
Unit/Run Numbers: FY28014
Operator ID:  KD                     Machine ID:    10137

===============================================================================

| TIME | AC FLOW VOL | INLET FLOW VOL | PLASMA FLOW VOL | COLLECT FLOW VOL | AC RATIO | YIELD PLT PR |
|---|---|---|---|---|---|---|
| 14:52:52 | NOTE: | – – – Start of data logging | | | | |
| 18:03:47 | NOTE: | – – – Exiting PAUSED mode | | | | |
| 18:03:47 | ALARM: | Restarting centrifuge. | | | | |
| 18:03:47 | CLEARED: | Restarting centrifuge. | | | | |
| 18:03:47 | NOTE: | – – – Start of Procedure Run | | | | |
| 18:05:39 | ALARM: | ACCESS PRESSURE LOW! | | | | |
|  |  | Check access line and needle. | | CONTINUE | | |
| 18:05:29 | CLEARED: | ACCESS PRESSURE LOW! | | | | |
|  |  | Check access line and needle. | | CONTINUE | | |
| 18:05:35 | NOTE: | – – – Entering PAUSED mode | | | | |
| 18:05:41 | NOTE: | – – – Exiting PAUSED mode | | | | |
| 18:05:41 | ALARM: | ACCESS PRESSURE LOW! | | | | |
|  |  | Check access line and needle. | | CONTINUE | | |
| 18:05:47 | CLEARED: | ACCESS PRESSURE LOW! | | | | |
|  |  | Check access line and needle. | | CONTINUE | | |
| 18:05:59 | NOTE: | – – – Entering PAUSED mode | | | | |
| 18:06:05 | NOTE: | – – – Exiting PAUSED mode | | | | |
| 18:06:05 | ALARM: | ACCESS PRESSURE LOW! | | | | |
|  |  | Check access line and needle. | | CONTINUE | | |
| 18:06:05 | CLEARED: | ACCESS PRESSURE LOW! | | | | |
|  |  | Check access line and needle. | | CONTINUE | | |
| 18:06:17 | NOTE: | – – – Entering PAUSED mode | | | | |
| 18:06:23 | NOTE: | – – – Exiting PAUSED mode | | | | |
| 18:06:23 | ALARM: | ACCESS PRESSURE LOW! | | | | |
|  |  | Check access line and needle. | | CONTINUE | | |
| 18:06:23 | CLEARED: | ACCESS PRESSURE LOW! | | | | |
|  |  | Check access line and needle. | | CONTINUE | | |
| 18:07:29 | ALARM: | Close return saline. Press CLEAR. | | | | |
| 18:07:29 | CLEARED: | Close return saline. Press CLEAR. | | | | |
| 19:09:18 | NOTE: | – – – Entering PAUSED mode | | | | |
| 19:09:24 | NOTE: | – – – Exiting PAUSED mode | | | | |
| 19:09:24 | ALARM: | ACCESS PRESSURE LOW! | | | | |
|  |  | Check access line and needle. | | CONTINUE | | |
| 19:09:24 | CLEARED: | ACCESS PRESSURE LOW! | | | | |
|  |  | Check access line and needle. | | CONTINUE | | |
| 19:10:48 | NOTE: | – – – Entering PAUSED mode | | | | |
| 19:10:54 | ALARM: | ACCESS PRESSURE LOW! | | | | |
|  |  | Check access line and needle. | | CONTINUE | | |

FIG. 13B

PROCEDURE MACHINE REPORT
Page 3
09/21/94
Name:    ANDREA          ID Number: ?
10:44:32
Social Security Number: 445-66-8855     Birth Date (mm/dd/yy):  12/13/63

Run Date: 09/20/94    Time: 20:08:10
Unit/Run Numbers: FY28014
Operator ID: KD                    Machine ID:     10137
================================================================================

| TIME | AC FLOW | AC VOL | INLET FLOW | INLET VOL | PLASMA FLOW | PLASMA VOL | COLLECT FLOW | COLLECT VOL | AC RATIO | YIELD PLT PR |
|------|---------|--------|------------|-----------|-------------|------------|--------------|-------------|----------|--------------|
| ---- | ------- | ------ | ---------- | --------- | ----------- | ---------- | ------------ | ----------- | -------- | ------------ |

| 19:10:54 | CLEARED: | ACCESS PRESSURE LOW! |
| | | Check access line and needle. | CONTINUE |
| 19:11:06 | NOTE: | – – – Exiting PAUSED mode |
| 19:19:30 | ALARM: | End of run:  1=Rinseback,  2=Continue Run |
| | | |
| 19:20:00 | NOTE: | – – – Entering PAUSED mode |
| 19:20:06 | CLEARED: | End of run:  1=Rinseback,  2=Continue Run |
| | | |
| 19:20:18 | NOTE: | – – – Exiting PAUSED mode |
| 19:22:00 | ALARM: | Clamp and disconnect connection bags. |
| | | Press CLEAR. |
| 19:22:00 | CLEARED: | Clamp and disconnect connection bags. |
| | | Press CLEAR. |
| 19:28:49 | NOTE: | – – – Entering PAUSED mode |
| 20:08:07 | NOTE: | – – – End of Run detected |
| 20:09:19 | NOTE: | – – – Run data saved to diskette |

– – – – Alarm Summary – – – –

| nt | Alarm |
|----|-------|
| | |
| 6 | ACCESS PRESSURE LOW! |
| | Check access line and needle.          CONTINUE |
| 1 | End of run:  1=Rinseback,  2=Continue Run |
| | |
| 1 | |
| | Close return saline.  Press CLEAR. |
| 1 | Clamp and disconnect connection bags. |
| | Press CLEAR. |
| 1 | |
| | Restarting centrifuge. |

FIG. 14A

APOLLOnet – Automated Data Management System  Page 1
 09/21/94
RUN DATA REPORT 10:41:55

HEALTH SYSTEMS-BLD DONOR SERVICES
3289 WOODBURN RD.

Name:     JAMES     ID Number: ?
Social Security Number: 137-32-9951     Birth Date (mm/dd/yy): 12/09/39

Run Date: 09/21/94     Time: 09:45:59
Unit/Run Numbers: FY28026
Operator ID: KJ     Machine ID:     10137
================================================================

– – PROCEDURE END – –

Procedure:     PLATELET
    Dual Needle?:     Y

Start Time:     08:05
    Stop Time:     09:45

– – VITALS – –

Blood Pressure (mmHg):     138/ 90
Temperature (F):     97.8
Pulse (/min):     56
Height (ft):     6' 0"
Weight (lb):     190
Total Blood Volume (ml):     5622
Blood Type:     *     A+
CMV:     *     +
Sex:     *     M

– – HEMATOLOGY – –

RBC Count (E6/ul):     4.9
HGB (g/dl):     14.6
Hct (%):     44
PLT Count (E3/ul):     238
WBC Count (/ul):     5.6

FIG. 14B

RUN DATA REPORT

Page 2
09/21/94
10:41:55

Name: JAMES ID Number: ?
Social Security Number: 137-32-9951 Birth Date (mm/dd/yy): 12/09/39

Run Date: 09/21/94 Time: 09:45:59
Unit/Run Numbers: FY28026
Operator ID: KJ Machine ID: 10137

==================================================================================

-- RUN RESULTS (PLATELET) --

| | |
|---|---|
| PLT Yield (E11): | 4.2 |
| CCM Yield (E11): | 7.2 |
| PLT Collect Conc. (E3/ul): | 1357 |
| PLT Volume (ml): | 310 |
| AC in PLT Volume (ml): | 57 |
| Net PLT Volume (ml): | 253 |
| Plasma Volume (ml): | 0 |
| AC in Plasma Volume (ml): | 0 |
| Net Plasma Volume (ml): | 0 |
| Inlet/AC Ratio Method: | M |
| AC Infusion Rate (ml/min/1BV): | 0.9 |
| Inlet Volume incl. AC (ml): | 4151 |
| AC Volume (ml): | 471 |
| Run Time (min): | 85.1 |

Disposables Used:

| Lot Number | Type | Exp Date Mo | Yr | Manufacturer |
|---|---|---|---|---|
| 07715263 | TUBING | 07 | 96 | COBE |
| C264804 | ACDA-A | 12 | 95 | BAXTER |
| C268607 | SALINE | 02 | 96 | BAXTER |

Procedure Notes:

FIG. 14C

RUN DATA REPORT

Page 3
09/21/94
10:41:55

Name:   JAMES         ID Number:  ?
Social Security Number:  137-32-9951      Birth Date (mm/dd/yy): 12/09/39

Run Date: 09/21/94   Time: 09:45:59
Unit/Run Numbers: FY28026
Operator ID: KJ                                      Machine ID:    10137

| TIME | AC FLOW | AC VOL | INLET FLOW | INLET VOL | PLASMA FLOW | PLASMA VOL | COLLECT FLOW | COLLECT VOL | AC RATIO | YIELD PLT PR |
|---|---|---|---|---|---|---|---|---|---|---|
| 20:09:34 | NOTE: | | – – – Start of data logging | | | | | | | |
| 20:25:37 | NOTE: | | – – – Exiting PAUSED mode | | | | | | | |
| 20:25:43 | NOTE: | | – – – Entering PAUSED mode | | | | | | | |
| 07:36:38 | NOTE: | | – – – Logging Resumed After Abnormal Program Termination | | | | | | | |
| 07:36:55 | ALARM: | | POWER INTERRUPTED! Continue with previous procedure (YES/NO)? | | | | | | | |
| 07:36:55 | CLEARED: | | POWER INTERRUPTED! Continue with previous procedure (YES/NO)? | | | | | | | |
| 07:36:55 | 0.0 | 47 | 0.0 | 504 | 0.0 | 85 | 0.0 | 8 | 0.0 | 0.00 |
| 08:05:43 | NOTE: | | – – – Exiting PAUSED mode | | | | | | | |
| 08:05:43 | NOTE: | | – – – Start of Procedure Run | | | | | | | |
| 08:05:43 | 5.1 | 0 | 45.0 | 1 | 14.4 | 0 | 3.5 | 0 | 8.9 | 4.73 |
| 08:05:49 | ALARM: | | Restarting centrifuge. | | | | | | | |
| 08:05:49 | CLEARED: | | Restarting centrifuge. | | | | | | | |
| 08:05:49 | 5.1 | 1 | 45.0 | 6 | 14.4 | 0 | 3.5 | 0 | 8.9 | 4.73 |
| 08:08:07 | 3.0 | 12 | 30.0 | 109 | 0.0 | 0 | 0.0 | 0 | 8.9 | 4.73 |
| 08:08:13 | 5.1 | 12 | 45.0 | 109 | 14.4 | 0 | 3.5 | 0 | 8.9 | 4.72 |
| 08:08:19 | ALARM: | | Close return saline. Press CLEAR. | | | | | | | |
| 08:08:19 | CLEARED: | | Close return saline. Press CLEAR. | | | | | | | |
| 08:08:19 | 5.1 | 13 | 45.0 | 113 | 14.4 | 0 | 3.5 | 0 | 8.9 | 4.72 |
| 08:10:19 | 5.1 | 23 | 45.0 | 203 | 14.4 | 0 | 3.5 | 0 | 8.9 | 4.72 |
| 08:15:07 | 5.1 | 47 | 45.0 | 419 | 14.2 | 0 | 3.8 | 16 | 8.9 | 5.03 |
| 08:15:13 | 5.1 | 48 | 45.0 | 423 | 14.1 | 0 | 3.8 | 17 | 8.9 | 4.31 |
| 08:17:01 | 5.6 | 57 | 50.2 | 505 | 5.0 | 0 | 3.8 | 24 | 8.9 | 4.31 |
| 08:18:43 | NOTE: | | – – – Entering PAUSED mode | | | | | | | |
| 08:18:43 | 5.6 | 66 | 50.2 | 588 | 5.0 | 0 | 3.8 | 30 | 8.9 | 4.31 |
| 08:18:49 | ALARM: | | ACCESS PRESSURE LOW! Check access line and needle. | | | | | CONTINUE | | |
| 08:18:49 | 5.6 | 66 | 50.2 | 588 | 5.0 | 0 | 3.8 | 30 | 8.9 | 4.31 |
| 08:18:55 | NOTE: | | – – – Exiting PAUSED mode | | | | | | | |
| 08:18:55 | 5.6 | 66 | 50.2 | 588 | 5.0 | 0 | 3.8 | 30 | 8.9 | 4.31 |
| 08:19:01 | CLEARED: | | ACCESS PRESSURE LOW! Check access line and needle. | | | | | CONTINUE | | |
| 08:19:01 | 5.6 | 67 | 50.2 | 591 | 5.0 | 0 | 3.8 | 30 | 8.9 | 4.31 |
| 08:20:43 | 5.6 | 76 | 50.2 | 676 | 5.0 | 0 | 3.8 | 37 | 8.9 | 4.31 |
| 08:25:01 | NOTE: | | – – – Entering PAUSED mode | | | | | | | |
| 08:25:01 | 5.6 | 101 | 50.2 | 892 | 5.0 | 0 | 3.8 | 53 | 8.9 | 4.31 |
| 08:25:07 | NOTE: | | – – – Exiting PAUSED mode | | | | | | | |
| 08:25:07 | ALARM: | | ACCESS PRESSURE LOW! Check access line and needle. | | | | | CONTINUE | | |

FIG. 14D

RUN DATA REPORT

Page 4
09/21/94
10:41:55

Name: JAMES  ID Number: ?
Social Security Number: 137-32-9951  Birth Date (mm/dd/yy): 12/09/39

Run Date: 09/21/94  Time: 09:45:59
Unit/Run Numbers: FY28026
Operator ID: KJ  Machine ID: 10137

| TIME | AC FLOW | AC VOL | INLET FLOW | INLET VOL | PLASMA FLOW | PLASMA VOL | COLLECT FLOW | COLLECT VOL | AC RATIO | YIELD PLT PR |
|---|---|---|---|---|---|---|---|---|---|---|
| 08:25:07 | 5.6 | 101 | 50.2 | 892 | 5.0 | 0 | 3.8 | 53 | 8.9 | 4.31 |
| 08:25:13 | CLEARED: | | ACCESS PRESSURE LOW! | | | | | | | |
| | | | Check access line and needle. | | | | CONTINUE | | | |
| 08:25:13 | 5.6 | 101 | 50.2 | 894 | 5.0 | 0 | 3.8 | 53 | 8.9 | 4.31 |
| 08:29:20 | NOTE: | | − − − Entering PAUSED mode | | | | | | | |
| 08:29:20 | 5.6 | 124 | 50.2 | 1100 | 5.0 | 0 | 3.8 | 69 | 8.9 | 4.31 |
| 08:29:25 | NOTE: | | − − − Exiting PAUSED mode | | | | | | | |
| 08:29:25 | ALARM: | | ACCESS PRESSURE LOW! | | | | | | | |
| | | | Check access line and needle. | | | | CONTINUE | | | |
| 08:29:25 | 5.6 | 124 | 50.2 | 1101 | 5.0 | 0 | 3.8 | 69 | 8.9 | 4.31 |
| 08:29:31 | CLEARED: | | ACCESS PRESSURE LOW! | | | | | | | |
| | | | Check access line and needle. | | | | CONTINUE | | | |
| 08:29:31 | 5.6 | 125 | 50.2 | 1105 | 5.0 | 0 | 3.8 | 70 | 8.9 | 4.31 |
| 08:35:44 | 5.6 | 160 | 50.2 | 1417 | 5.0 | 0 | 3.8 | 93 | 8.9 | 4.31 |
| 08:37:02 | NOTE: | | − − − Entering PAUSED mode | | | | | | | |
| 08:37:02 | 5.6 | 167 | 50.2 | 1479 | 5.0 | 0 | 3.8 | 98 | 8.9 | 4.31 |
| 08:37:08 | ALARM: | | ACCESS PRESSURE LOW! | | | | | | | |
| | | | Check access line and needle. | | | | CONTINUE | | | |
| 08:37:08 | CLEARED: | | ACCESS PRESSURE LOW! | | | | | | | |
| | | | Check access line and needle. | | | | CONTINUE | | | |
| 08:37:08 | 5.6 | 167 | 50.2 | 1479 | 5.0 | 0 | 3.8 | 98 | 8.9 | 4.31 |
| 08:37:20 | NOTE: | | − − − Exiting PAUSED mode | | | | | | | |
| 08:37:20 | 5.6 | 167 | 50.2 | 1480 | 5.0 | 0 | 3.8 | 98 | 8.9 | 4.31 |
| 08:41:50 | NOTE: | | − − − Entering PAUSED mode | | | | | | | |
| 08:41:50 | 5.6 | 192 | 50.2 | 1704 | 5.0 | 0 | 3.8 | 115 | 8.9 | 4.30 |
| 08:41:56 | ALARM: | | ACCESS PRESSURE LOW! | | | | | | | |
| | | | Check access line and needle. | | | | CONTINUE | | | |
| 08:41:56 | CLEARED: | | ACCESS PRESSURE LOW! | | | | | | | |
| | | | Check access line and needle. | | | | CONTINUE | | | |
| 08:41:56 | 5.6 | 192 | 50.2 | 1704 | 5.0 | 0 | 3.8 | 115 | 8.9 | 4.30 |
| 08:42:08 | NOTE: | | − − − Exiting PAUSED mode | | | | | | | |
| 08:42:08 | 5.6 | 193 | 50.2 | 1704 | 5.0 | 0 | 3.8 | 115 | 8.9 | 4.30 |
| 08:44:26 | NOTE: | | − − − Entering PAUSED mode | | | | | | | |
| 08:44:26 | 5.6 | 205 | 50.2 | 1815 | 5.0 | 0 | 3.8 | 124 | 8.9 | 4.31 |
| 08:44:32 | ALARM: | | ACCESS PRESSURE LOW! | | | | | | | |
| | | | Check access line and needle. | | | | CONTINUE | | | |
| 08:44:32 | CLEARED: | | ACCESS PRESSURE LOW! | | | | | | | |
| | | | Check access line and needle. | | | | CONTINUE | | | |
| 08:44:32 | 5.6 | 205 | 50.2 | 1815 | 5.0 | 0 | 3.8 | 124 | 8.9 | 4.31 |
| 08:44:38 | NOTE: | | − − − Exiting PAUSED mode | | | | | | | |
| 08:44:38 | 5.6 | 205 | 50.2 | 1816 | 5.0 | 0 | 3.8 | 124 | 8.9 | 4.31 |
| 08:50:44 | 5.6 | 240 | 50.2 | 2123 | 5.0 | 0 | 3.8 | 148 | 8.9 | 4.30 |
| 08:52:20 | NOTE: | | − − − Entering PAUSED mode | | | | | | | |
| 08:52:20 | 5.6 | 249 | 50.2 | 2201 | 5.0 | 0 | 3.8 | 154 | 8.9 | 4.30 |
| 08:52:26 | ALARM: | | ACCESS PRESSURE LOW! | | | | | | | |

FIG. 15A

APOLLOnet – Automated Data Management System

Page 1
10/19/94
12:17:30

DONOR/PATIENT PROCEDURE REPORT

COBE BCT
1201 OAK ST.

Name: BERRA, YOGI     ID Number: 7290-5600
Social Security Number: 123-45-6789     Birth Date (mm/dd/yy): 11/04/26

Procedures included in this report: last procedure only

Run Date: 09/07/94    Time: 14:38:34
Unit/Run Numbers: 1212121212
Operator ID: DEL                      Machine ID:    0

– – PROCEDURE (DONOR/PATIENT) – –

| | |
|---:|:---|
| Procedure: | PLATELET |
| Dual Needle?: | Y |
| Collect Plasma?: | Y |
| Access Needle: | 18 |
| Return Needle: | 18 |
| Access Site: | LEFT FEMORAL |
| Return Site: | RIGHT FEMORAL |
| Allergy: | POLLEN |
| Target Run Time (min): | 119 |
| Data Recording Interval (min): | 6 |
| Inlet/AC Ratio Method: | L |
| Inlet/AC Ratio    : | 7.4 |

– MAXIMUM FLOW RATES –

| | |
|---:|:---|
| SN Inlet (ml/min): | 45.0 |
| DN Inlet (ml/min): | 49.0 |
| AC Infusion (ml/min/1BV): | 1.1 |

– – THERAPEUTICS – –

| | |
|---:|:---|
| Disease: | MULTIPLE SCLEROSIS |
| Bleeding Time (min): | 3.0 |
| Respiration (/min): | 14 |
| Plasma Volume (ml): | 2758 |
| Replacement Volume (ml): | 221 |
| Fluid Balance (%): | 110.0 |

– RED BLOOD CELL EXCHANGE –

| | |
|---:|:---|
| Avg. Replacement Hct (%): | 87 |
| End Hct (%): | 69 |
| FCR (%): | 43 |

FIG. 15B

DONOR/PATIENT PROCEDURE REPORT  Page 2
 10/19/94
Name: BERRA, YOGI  ID Number: 7290-5600  12:17:30
Social Security Number: 123-45-6789  Birth Date (mm/dd/yy): 11/04/26

Run Date: 09/07/94  Time: 14:38:34
Unit/Run Numbers: 1212121212
Operator ID: DEL  Machine ID: 0

================================================================================

-- PROCEDURE END --

Procedure: PLATELET
Dual Needle?: Y

Start Time: ??:??
Stop Time: 14:38

-- VITALS --
Blood Pressure (mmHg): 110/ 70
Temperature (F): 98.5
Pulse (/min): 65
Height (ft): 5' 11"
Weight (lb): 188
Total Blood Volume (ml): 5091
Blood Type: * A+
CMV: * +
Sex: * M -- HEMATOLOGY --
RBC Count (E6/ul): 4.2
HGB (g/dl): 14.0
Hct (%): 55
PLT Count (E3/ul): 1234
WBC Count (/ul): 7.0

. . . . . . . . . . . . . . . . . . . . . . . . . . . . . . . . . . . . . . . . . . . . . . . . . . . .

-- RUN RESULTS (PLATELET) --

PLT Yield (E11): 2.0
CCM Yield (E11): 4.9
PLT Collect Conc. (E3/ul): 0

PLT Volume (ml): 400
AC in PLT Volume (ml): 800
Net PLT Volume (ml): -400

Plasma Volume (ml): 500
AC in Plasma Volume (ml): 100
Net Plasma Volume (ml): 400

Inlet/AC Ratio Method: L
AC Infusion Rate (ml/min/1BV): 1.1
Inlet Volume incl. AC (ml): 6000
AC Volume (ml): 600

Run Time (min): 100.0

Disposables Used:

FIG. 15C

DONOR/PATIENT PROCEDURE REPORT

Page 3
10/19/94
12:17:30

Name: BERRA, YOGI ID Number: 7290-5600
Social Security Number: 123-45-6789 Birth Date (mm/dd/yy): 11/04/26

Run Date: 09/07/94 Time: 14:38:34
Unit/Run Numbers: 1212121212
Operator ID: DEL Machine ID: 0

===============================================================================

No Entries.

Procedure Notes:

FIG. 15D

DONOR/PATIENT PROCEDURE REPORT

Page 4
10/19/94
12:17:30

Name: BERRA, YOGI   ID Number: 7290-5600
Social Security Number: 123-45-6789   Birth Date (mm/dd/yy): 11/04/26

Run Date: 09/07/94   Time: 14:38:34
Unit/Run Numbers: 1212121212
Operator ID: DEL   Machine ID: 0

| TIME | AC FLOW | AC VOL | INLET FLOW | INLET VOL | PLASMA FLOW | PLASMA VOL | COLLECT FLOW | COLLECT VOL | AC RATIO | YIELD PLT PR |
|---|---|---|---|---|---|---|---|---|---|---|
| 14:28:55 | NOTE: | | – – – Start of data logging | | | | | | | |
| 14:37:33 | 10.0 | 0 | 50.0 | 0 | 20.0 | 0 | 30.0 | 0 | 0.0 | 0.00 |
| 14:37:45 | 10.0 | 120 | 51.0 | 1200 | 20.0 | 100 | 30.0 | 80 | 1.5 | 4.67 |
| 14:37:50 | ALARM: | | FAILURE # 1: Display Processor – ___ | | | | | | | |
| | | | Record #. CONTINUE to retry or Rinse. * | | | | | | | |
| 14:37:50 | 10.0 | 180 | 51.0 | 1800 | 20.0 | 150 | 30.0 | 120 | 2.2 | 4.33 |
| 14:37:56 | 10.0 | 240 | 52.0 | 2400 | 20.0 | 200 | 30.0 | 160 | 3.0 | 4.00 |
| 14:38:08 | 10.0 | 360 | 53.0 | 3600 | 20.0 | 300 | 30.0 | 240 | 4.4 | 3.33 |
| 14:38:14 | CLEARED: | | FAILURE # 1: Display Processor – ___ | | | | | | | |
| | | | Record #. CONTINUE to retry or Rinse. * | | | | | | | |
| 14:38:14 | 10.0 | 420 | 53.0 | 4200 | 20.0 | 350 | 30.0 | 280 | 5.2 | 3.00 |
| 14:38:20 | 10.0 | 480 | 54.0 | 4800 | 20.0 | 400 | 30.0 | 320 | 5.9 | 2.67 |
| 14:38:32 | NOTE: | | – – – End of Run detected | | | | | | | |
| 14:38:32 | 10.0 | 600 | 55.0 | 6000 | 20.0 | 500 | 30.0 | 400 | 7.4 | 2.00 |
| 14:50:39 | NOTE: | | – – – Run data saved to diskette | | | | | | | |

FIG. 16

APOLLOnet - Automated Data Management System

DONOR/PATIENT HISTORY REPORT

Page 1
10/19/94
12:19:46

COBE BCT
1201 OAK ST.

Name: BERRA, YOGI     ID Number: 7290-5600
Social Security Number: 123-45-6789     Birth Date (mm/dd/yy): 11/04/26

Procedures included in this report: all procedures

| | | | | |
|---:|---:|---:|---:|---:|
| Date (mm/dd/yy): | 09/07/94 | 09/07/94 | 09/07/94 | Average |
| Procedure: | PLATELET | PLATELET | PLATELET | --------- |
| Machine ID: | 0 | 0 | 0 | |
| Run Time (min): | 100.0 | 100.0 | 100.0 | 100.0 |
| PLT Yield (E11): | 2.0 | 2.0 | 2.0 | 2.0 |
| PLT Collect Conc. (E3/ul): | 0 | 0 | 0 | 0 |
| PLT Volume (ml): | 400 | 400 | 400 | 400 |
| Plasma Volume (ml): | 500 | 500 | 500 | 500 |
| Nominal RBC Loss (ml): | 10.5 | 10.5 | 10.5 | 10.5 |
| Blood Pressure (mmHg): | 110/ 70 | 111/ 60 | * 111/ 60 | 111/ 65 |
| Temperature F): | 98.5 | 98.6 | * 98.6 | 98.6 |
| Pulse (/min): | 65 | 66 | * 66 | 66 |
| Height (ft): | 5' 11" | 5' 11" | 5' 11" | 5' 11" |
| Weight (lb): | 188 | 188 | 188 | 188 |
| RBC Count (E6/ul): | 4.2 | 5.0 | * 5.0 | 4.6 |
| HGB (g/dl): | 14.0 | 15.0 | * 15.0 | 14.5 |
| Hct (%): | 55 | 55 | 55 | 55 |
| PLT Count E3/ul): | 1234 | 1234 | 1234 | 1234 |
| WBC Count (/ul): | 7.0 | 8.0 | * 8.0 | 7.5 |
| Hct, Post (%): | 43 | 44 | * 44 | 44 |
| PLT Postcount (E3/ul): | 299 | 300 | * 300 | 300 |
| Total Blood Volume (ml): | 5091 | 5091 | 5091 | 5091 |

Total Nominal RBC Loss (ml): 31.5
Averages are based on confirmed values from the last 3 procedures.

FIG. 17A

APOLLOnet – Automated Data Management System      Page 1
09/21/94
PLT PRODUCTION REPORT      10:46:58

HEALTH SYSTEMS–BLD DONOR SERVICES
3289 WOODBURN RD.
===========================================================================

Report Period:
Start Date (mm/dd/yy): 09/20/94
Stop Date (mm/dd/yy): / /

Unit Yield Definitions
(for this report only):
SDP (E11): 4.0
DPP (E11): 6.8

– SPECTRA RUNS –

|  | SDP | DPP | Total SDP and DPP |
|---|---|---|---|
| Number of Runs | 15 | 6 | 21 |
| % of Total Runs | 71% | 29% | 100% |
| Runs Exceeding Unit Yield | 14 | 6 | 20 |
| % Exceeding Unit Yield | 93% | 100% | 95% |

Avg. Run Results:

|  | SDP | DPP | Total SDP and DPP |
|---|---|---|---|
| PLT Yield (E11) | 4.1 | 7.1 | 4.9 |
| CCM Yield (E11) | 4.8 | 6.6 | 5.4 |
| Collect Volume (ml) | 197 | 344 | 239 |
| PLT Collect Conc. (E3/ul) | 1262 | 1363 | 1291 |
| CCM Collect Conc. (E3/ul) | 1379 | 988 | 1267 |
| Run Time (min) | 85 | 93 | 87 |
| Number of Plasma Runs | 0 | 0 | 0 |
| Plasma Volume (ml) | 0 | 0 | 0 |

Avg. Lab Results:

|  | SDP | DPP | Total SDP and DPP |
|---|---|---|---|
| Number of Lab Totals | 7 | 5 | 12 |
| PLT Count (E11) | 4.0 | 7.1 | 5.3 |
| RBC Count (%) | 0.1 | 0.1 | 0.1 |
| WBC Count (E11) | 0.0 | 0.0 | 0.0 |
| Collect Volume (ml) | 320 | 520 | 403 |
| PLT Collect Conc. (E3/ul) | 1239 | 1363 | 1291 |
| Plasma Volume (ml) | 0 | 0 | 0 |

FIG. 17B

APOLLOnet – Automated Data Management System

PLT PRODUCTION REPORT

HEALTH SYSTEMS-BLD DONOR SERVICES
3289 WOODBURN RD.

Page 2
09/21/94
10:46:58

– NON-SPECTRA RUNS –

|  | SDP | DPP | Total SDP and DPP |
|---|---|---|---|
| Number of Runs | 0 | 0 | 0 |
| % of Total Runs | 0% | 0% | 0% |
| Runs Exceeding Unit Yield | 0 | 0 | 0 |
| % Exceeding Unit Yield | 0% | 0% | 0% |

Avg. Run Results:

|  | SDP | DPP | Total SDP and DPP |
|---|---|---|---|
| PLT Yield (E11) | 0.0 | 0.0 | 0.0 |
| Collect Volume (ml) | 0 | 0 | 0 |
| PLT Collect Conc. (E3/ul) | 0 | 0 | 0 |
| Run Time (min) | 0 | 0 | 0 |
| Number of Plasma Runs | 0 | 0 | 0 |
| Plasma Volume (ml) | 0 | 0 | 0 |

Avg. Lab Results:

|  | SDP | DPP | Total SDP and DPP |
|---|---|---|---|
| Number of Lab Totals | 0 | 0 | 0 |
| PLT Count (E11) | 0.0 | 0.0 | 0.0 |
| RBC Count (%) | 0.0 | 0.0 | 0.0 |
| WBC Count (E11) | 0.0 | 0.0 | 0.0 |
| Collect Volume (ml) | 0 | 0 | 0 |
| PLT Collect Conc. (E3/ul) | 0 | 0 | 0 |
| Plasma Volume (ml) | 0 | 0 | 0 |

FIG. 17C

APOLLOnet – Automated Data Management System

PLT PRODUCTION REPORT

Page 3
09/21/94
10:46:58

HEALTH SYSTEMS-BLD DONOR SERVICES
3289 WOODBURN RD.

– TOTAL RUNS –

|  | SDP | DPP | Total SDP and DPP |
|---|---|---|---|
| Number of Runs | 15 | 6 | 21 |
| % of Total Runs | 71% | 29% | 100% |
| Runs Exceeding Unit Yield | 14 | 6 | 20 |
| % Exceeding Unit Yield | 93% | 100% | 95% |

Avg. Run Results:

|  | SDP | DPP | Total SDP and DPP |
|---|---|---|---|
| PLT Yield (E11) | 4.1 | 7.1 | 4.9 |
| Collect Volume (ml) | 197 | 344 | 239 |
| PLT Collect Conc. (E3/ul) | 1262 | 1363 | 1291 |
| Run Time (min) | 85 | 93 | 87 |
| Number of Plasma Runs | 0 | 0 | 0 |
| Plasma Volume (ml) | 0 | 0 | 0 |

Avg. Lab Results:

|  | SDP | DPP | Total SDP and DPP |
|---|---|---|---|
| Number of Lab Totals | 7 | 5 | 12 |
| PLT Count (E11) | 4.0 | 7.1 | 5.3 |
| RBC Count (%) | 0.1 | 0.1 | 0.1 |
| WBC Count (E11) | 0.0 | 0.0 | 0.0 |
| Collect Volume (ml) | 320 | 520 | 403 |
| PLT Collect Conc. (E3/ul) | 1239 | 1363 | 1291 |
| Plasma Volume (ml) | 0 | 0 | 0 |

FIG. 18

```
APOLLOnet - Automated Data Management System                    Page    1
                                                                09/21/94
STAFF REPORT                                                    10:50:42

HEALTH SYSTEMS-BLD DONOR SERVICES
3289 WOODBURN RD.
==========================================================================

Report Period:
               Start Date  (mm/dd/yy):       / /
                Stop Date  (mm/dd/yy):       / /

Name                          Oper ID   Number of runs
---------------------------   -------   --------------

ALAN J                        AJH              2
CAROL R.                      CRS              0
CHERYL                        CLK              0
CHRISTINE                     CD               2
JESSICA                       JS               4
KAREN                         KL               1
KATHLEEN                      KD               6
KIMBERLY                      KJ               2
SARA                          SS               4
TERRI                         TLC              0
(unknown operator ID)                          0
--------------------------------------------------------------
                                     Total:   21
```

FIG. 19

```
APOLLOnet - Automated Data Management System          Page    1
                                                      09/21/94
DM STATISTICS REPORT                                  11:03:22

HEALTH SYSTEMS-BLD DONOR SERVICES
3289 WOODBURN RD.
================================================================

PERSONS

Donors:  88
                    Patients:  0
           Donor and Patient:  0
    New Donor/Patient (no runs):  11

Number of People:  99

PROCEDURES

- - - - Donor - - - -
         PlateletDual Needle:  21
      Platelet Single Needle:  0
         WBC/PMN Dual Needle:  0

- - - - Patient - - - -
    WBC/PMN      Dual Needle:  0
    WBC/MNC      Dual Needle:  0
    TPE          Dual Needle:  0
    TPE        Single Needle:  0
    PLT Depl     Dual Needle:  0
    RBCX         Dual Needle:  0
    WBC/BMP                :  0

Undefined:  0

Total Procedures:  21

PM procedure orders:  0
         DM procedure orders:  21

Spectra procedures:  21
       Non-Spectra procedures:  0
```

FIG. 20A

APOLLOnet - Automated Data Management System    Page 1
                                                10/19/94
DONOR/PATIENT LIST                              12:22:03

COBE BCT
1201 OAK ST.
================================================================================

- SEARCH CRITERIA -

Include Donors?: Y
Include Patients?: Y
Include New Persons (no runs)?: Y

City:
State:

Last Procedure Date (mm/dd/yy):
Oldest Acceptable:    / /
Most Recent Acceptable:    / /

Last Procedure:

Sort order: Last Procedure Date
--------------------------------------------------------------------------------
Name: BERRA, YOGI                                                        ID Number: 7290-5600
    Address: 645 CATCHER'S LANE                ?
    City: NEW YORK              State: NY     Zip: 08679
    Phone: (Home) (213) 222-3333 /4444         (Work) (213) 666-7777 /8888
    Donor: Y    Patient: N    Last Procedure:                           Date:   / /

Name: WAZ I, BACKED UP?                                                  ID Number: 1231231231
    Address: ?                                 ?
    City: LAKEWOOD              State: CO     Zip: ?
    Phone: (Home) ?                            (Work) ?
    Donor: N    Patient: N    Last Procedure:                           Date:   / /

Name: IBAAAC, TOM                                                        ID Number: 10002X
    Address: <- - - address 1 - - - - - - - - - - ->    <- - - address 2 - - - - - - - - - - - - - - - ->
    City: BOULDER               State: CO     Zip: 20344-1764
    Phone: (Home) (002) 555-1212 /1234         (Work) (002) 555-0123 /0000
    Donor: Y    Patient: N    Last Procedure: PLT [N/A]                 Date: 01/03/25

Name: HBAAAF, JUDY                                                       ID Number: 10005X
    Address: <- - - address 1 - - - - - - - - - - ->    <- - - address 2 - - - - - - - - - - - - - - - ->
    City: ARVADA                State: CO     Zip: 23112
    Phone: (Home) (005) 555-1212 /1234         (Work) (005) 555-0123 /0000
    Donor: N    Patient: Y    Last Procedure: WBC/MNC                   Date: 01/06/25

Name: HBAABD, JUDY                                                       ID Number: 10013X
    Address: <- - - address 1 - - - - - - - - - - ->    <- - - address 2 - - - - - - - - - - - - - - - ->
    City: ARVADA                State: CO     Zip: 23112
    Phone: (Home) (013) 555-1212 /1234         (Work) (013) 555-0123 /0000
    Donor: N    Patient: Y    Last Procedure: PLT DEPL                  Date: 01/14/25

FIG. 20B

```
                                                                          Page   2
DONOR/PATIENT LIST                                                        10/19/94
                                                                          12:22:03
================================================================================

Name: GBAABF, BUCK                                                  ID Number: 10016X
      Address:  <--- address 1 ----------->   <--- address 2 ------------------>
      City: DENVER            State: CO     Zip: 54321
      Phone: (Home) (016) 555-1212 /1234         (Work) (016) 555-0123 /0000
      Donor: N    Patient: Y    Last Procedure: WBC/PMN
                                                                    Date: 01/17/25

Name: EBAABI, DEBRA                                                 ID Number: 10018X
      Address:  <--- address 1 ----------->   <--- address 2 ------------------>
      City: GOLDEN            State: CO     Zip: 80401
      Phone: (Home) (018) 555-1212 /1234         (Work) (018) 555-0123 /0000
      Donor: N    Patient: Y    Last Procedure: WBC/BMP
                                                                    Date: 01/19/25

Name: FBAABJ, BOB                                                   ID Number: 10019X
      Address:  <--- address 1 ----------->   <--- address 2 ------------------>
      City: PARKER            State: CO     Zip:
      Phone: (Home) (019) 555-1212 /1234         (Work) (019) 555-0123 /0000
      Donor: N    Patient: Y    Last Procedure: UNKNOWN
                                                                    Date: 01/20/25

Name: GBAACA, BUCK                                                  ID Number: 10020X
      Address:  <--- address 1 ----------->   <--- address 2 ------------------>
      City: DENVER            State: CO     Zip: 54321
      Phone: (Home) (020) 555-1212 /1234         (Work) (020) 555-0123 /0000
      Donor: Y    Patient: N    Last Procedure: PLATELET
                                                                    Date: 01/21/25

Name: FBAACH, BOB                                                   ID Number: 10027X
      Address:  <--- address 1 ----------->   <--- address 2 ------------------>
      City: PARKER            State: CO     Zip:
      Phone: (Home) (027) 555-1212 /1234         (Work) (027) 555-0123 /0000
      Donor: N    Patient: Y    Last Procedure: PLT DEPL
                                                                    Date: 01/28/25

Name: GBAAAI, BUCK                                                  ID Number: 10008X
      Address:  <--- address 1 ----------->   <--- address 2 ------------------>
      City: DENVER            State: CO     Zip: 54321
      Phone: (Home) (008) 555-1212 /1234         (Work) (008) 555-0123 /0000
      Donor: Y    Patient: N    Last Procedure: PLT [N/A]
                                                                    Date: 01/31/25

Name: FBAADB, BOB                                                   ID Number: 10031X
      Address:  <--- address 1 ----------->   <--- address 2 ------------------>
      City: PARKER            State: CO     Zip:
      Phone: (Home) (031) 555-1212 /1234         (Work) (031) 555-0123 /0000
      Donor: N    Patient: Y    Last Procedure: WBC/BMP
                                                                    Date: 02/01/25

Name: HBAAAB, JUDY                                                  ID Number: 10001X
      Address:  <--- address 1 ----------->   <--- address 2 ------------------>
      City: ARVADA            State: CO     Zip: 23112
      Phone: (Home) (001) 555-1212 /1234         (Work) (001) 555-0123 /0000
      Donor: Y    Patient: Y    Last Procedure: PLATELET
                                                                    Date: 02/02/25

Name: EBAADI, DEBRA                                                 ID Number: 10038X
      Address:  <--- address 1 ----------->   <--- address 2 ------------------>
      City: GOLDEN            State: CO     Zip: 80401
      Phone: (Home) (038) 555-1212 /1234         (Work) (038) 555-0123 /0000
      Donor: N    Patient: Y    Last Procedure: WBC/BMP
                                                                    Date: 02/08/25
```

FIG. 21A

APOLLOnet - Automated Data Management System  Page 1
                                                09/21/94
DONOR SEARCH REPORT                             11:09:41

HEALTH SYSTEMS-BLD DONOR SERVICES
3289 WOODBURN RD.
================================================================================

- SEARCH CRITERIA -

Last Donation Date (mm/dd/yy):
                  Oldest Acceptable:  / /
            Most Recent Acceptable:  / /           HLA A:

HLA B:
                              City:
                            State:            HLA C:
                               Zip:

HLA D:
                       Area Code:

HLA DR:
                   Last Procedure:
           Minimum PLT Yield (E11): 7.0           HLA DQ:

Blood Type:           HLA DP:
                                CMV:

Sort order: Last procedure's true Yield

--------------------------------------------------------------------------------

Name:      LYNN                                                                 ID Number: ?
    Address: 3515 WASHINGTON BLVD
    City: ARLINGTON           State: VA     Zip: 22201
    Phone: (Home) 703-524-8078              (Work) ?
Last Donation Date: 09/01/94        Last Yield (E11): 7.70
Age: 67     Blood Type: A+    CMV: -
HLA:    A1: ?            A2: ?           B1: ?           B2: ?
       C1: ?            C2: ?           D1: ?           D2: ?
      DR1: ?           DR2: ?          DQ1: ?          DQ2: ?
      DP1: ?           DP2: ?

Name:      DOREEN                                                   ID Number: ?
    Address: 4897 WHEATSTONE DR.         ?
    City: FAIRFAX              State: VA     Zip: 22032
    Phone: (Home) 703-503-7178              (Work) 703-620-1489
Last Donation Date: 09/20/94        Last Yield (E11): 7.22
Age: 30     Blood Type: A-    CMV: -
HLA:    A1: ?            A2: ?           B1: ?           B2: ?
       C1: ?            C2: ?           D1: ?           D2: ?
      DR1: ?           DR2: ?          DQ1: ?          DQ2: ?
      DP1: ?           DP2: ?

FIG. 21B

DONOR SEARCH REPORT
Page 2
09/21/94
11:09:41
========================================================================

Name:      DIANE                                                          ID Number: ?
    Address: 8001 HOOS RD.                    ?
    City: SPRINGFIELD              State: VA  Zip: 22152
    Phone: (Home) 703-451-5661                (Work) ?
Last Donation Date: 09/20/94       Last Yield (E11): 7.20
Age: 40    Blood Type: A+   CMV: +
HLA:   A1: ?              A2: ?            B1: ?            B2: ?
       C1: ?              C2: ?            D1: ?            D2: ?
       DR1: ?             DR2: ?           DQ1: ?           DQ2: ?
       DP1: ?             DP2: ?

Name:      SUSAN                                                          ID Number: ?
    Address: 14437 GOLDEN OAK RD.             ?
    City: CENTREVILLE              State: VA  Zip: 22020
    Phone: (Home) 703-830-5532                (Work) 703-273-5120
Last Donation Date: 09/20/94       Last Yield (E11): 7.10
Age: 44    Blood Type: O+   CMV: −
HLA:   A1: ?              A2: ?            B1: ?            B2: ?
       C1: ?              C2: ?            D1: ?            D2: ?
       DR1: ?             DR2: ?           DQ1: ?           DQ2: ?
       DP1: ?             DP2: ?

Name:      JULES                                                          ID Number: ?
    Address: 8083 POWDER BROOK LN.            ?
    City: SPRINGFIELD              State: VA  Zip: 22153
    Phone: (Home) 703-455-8526                (Work) ?
Last Donation Date: 08/02/94       Last Yield (E11): 7.00
Age: 55    Blood Type: AB+  CMV: −
HLA:   A1: ?              A2: ?            B1: ?            B2: ?
       C1: ?              C2: ?            D1: ?            D2: ?
       DR1: ?             DR2: ?           DQ1: ?           DQ2: ?
       DP1: ?             DP2: ?

Name:      TODD                                                           ID Number: ?
    Address: 6906 HUNTSMAN BLVD.              ?
    City: SPRINGFIELD              State: VA  Zip: 22153
    Phone: (Home) 703-455-3159                (Work) 703-218-0496
Last Donation Date: 09/20/94       Last Yield (E11): 7.00
Age: 30    Blood Type: O+   CMV: −
HLA:   A1: ?              A2: ?            B1: ?            B2: ?
       C1: ?              C2: ?            D1: ?            D2: ?
       DR1: ?             DR2: ?           DQ1: ?           DQ2: ?
       DP1: ?             DP2: ?

FIG. 21C

DONOR SEARCH REPORT

Page 3
09/21/94
11:09:41

========================================================================

Name:     LOVETTA                                                    ID Number: ?
    Address: 3207 HEWITT ST.                    ?
    City: FALLS CHURCH         State: VA    Zip: 22042
    Phone: (Home) 703-573-6871              (Work) 703-698-3467
Last Donation Date: 08/23/94      Last Yield (E11): 7.00
Age: 50     Blood Type: O+     CMV:  +
HLA:    A1: ?               A2: ?           B1: ?           B2: ?
        C1: ?               C2: ?           D1: ?           D2: ?
        DR1: ?              DR2: ?          DQ1: ?          DQ2: ?
        DP1: ?              DP2: ?

Name:     RICHARD                                                    ID Number: ?
    Address: 513 LINDSAY CIYRT                  ?
    City: STERLING             State: VA    Zip: 20164
    Phone: (Home) 703-444-7160              (Work) 703-749-2650
Last Donation Date: 06/22/94      Last Yield (E11): 7.00
Age: 31     Blood Type: O+     CMV:  -
HLA:    A1: ?               A2: ?           B1: ?           B2: ?
        C1: ?               C2: ?           D1: ?           D2: ?
        DR1: ?              DR2: ?          DQ1: ?          DQ2: ?
        DP1: ?               DP2: ?

BLOOD COMPONENT COLLECTION SYSTEM WITH OPTIMIZER

RELATED APPLICATIONS

This application is a continuation-in-part of U.S. patent application Ser. No. 08/140,254, filed Oct. 21, 1993, and entitled "BLOOD COMPONENT COLLECTION SYSTEM WITH OPTIMIZER", which is a continuation-in-part of U.S. patent application Ser. No. 07/912,973, filed Jul. 10, 1992, entitled "METHOD AND APPARATUS FOR PRODUCING BLOOD COMPONENT PRODUCTS," now abandoned U.S. patent application Ser. No. 07/845,877, filed Mar. 4, 1992, now abandoned and U.S. patent application Ser. No. 08/110,432, now U.S. Pat. No. 5,437,624 filed Aug. 23, 1993, the entire disclosures of which are incorporated by reference herein.

FIELD OF THE INVENTION

The present invention generally relates to the field of blood component collection systems and, more particularly, to optimizing such systems.

BACKGROUND OF THE INVENTION

The utilization of blood taken from donors and infused into recipients is well known for purposes of treating medical emergencies and other conditions. More recently, selected blood components have been separated and collected from blood for subsequent infusion into recipients requiring blood component therapy. The primary blood components include platelets, red blood cells, white blood cells, and plasma.

In order to collect blood components, blood is removed from a donor by a needle assembly or other blood access device and is thereafter processed utilizing centrifugation or other appropriate separation techniques to isolate and collect the desired components. This procedure is carried out most effectively in an on-line process wherein blood is removed from a donor, processed through a disposable extracorporeal circuit to obtain the desired components, and thereafter returned to the donor. One blood component collection system which provides for this type of blood component collection procedure is the COBE Spectra™ which is commercially available from the assignee of the present application.

The yield of a particular collection of blood components is an important factor. For instance, presently in the U.S. a yield must be associated with a collection of blood components in order to be a useful blood component product. COBE Spectra™ presently accommodates for this requirement by processing certain donor biological data such as height, weight, sex, and hematocrit, preconfigured/operator-input data such as the total procedure time, and system-related data such as the type of collection procedure (e.g., single or double needle) and collection efficiency to generate certain process parameters such as the inlet flow to COBE Spectra™ (a combined flow of whole blood from the donor plus typically a flow of anticoagulant) and a predicted blood component yield as well.

An additional consideration presently in the U.S. relating to blood component yield is that it is determinative of the product classification. With regard to platelets, presently a single platelet product is considered to be a collection of $3 \times 10^{11}$ platelets and a double platelet product is considered to be a collection of $6 \times 10^{11}$ platelets. If the collection is between $3 \times 10^{11}$ and $6 \times 10^{11}$ platelets it is still considered to be a single platelet product. This classification as a single or double platelet product is relevant to blood component collection facilities (e.g., blood banks/centers) since a double platelet product has a higher selling price associated therewith than a single platelet product and also typically benefits more patients. The yield of a particular collection of blood components may also be a relevant consideration for certain therapeutic treatments.

Other important considerations relating to blood component collection systems relate to the donor. For instance, blood component collection facilities are not only experiencing an increase in the overall demand for blood components, but the demand now typically varies between the blood component types as well. Moreover, not only is the supply of donors unfortunately in many cases inadequate, but donor time constraints are becoming more prevalent. Furthermore, obtainable yields from a given donor may vary from one blood component to another (i.e., one donor may be a better platelet source than a red blood cell source).

Based upon the foregoing, the management of the various aspects of blood component collection systems is becoming increasingly important.

SUMMARY OF THE INVENTION

The present invention is generally directed toward optimizing blood component collection facilities operations. Generally, the present invention relates to a blood component collection system which performs blood component collection procedures and maintains various data on such collection procedures. As a result of the system configuration, such as the physical setup and/or the data collection, maintenance, transfer, and/or manipulation capabilities, blood component collection facility operations may be optimized.

The present invention more specifically relates to a blood component collection control and information communication system for use in conjunction with a blood component collection device. The procedure performed with this system and blood component collection device is the separation, removal, and collection of one or more types of blood components (e.g., platelets, red blood cells, white blood cells, plasma) from a source of blood (e.g., donors). Generally, this system includes first and second stations, at least one of which interfaces with the blood component collection device via an information communication medium. The first and second stations each have operator display and data input capabilities and each interact with the information communication medium regarding various data relating to collection procedures. Through appropriate utilization of this data, such as by generation, recordation, exchange, and manipulation of such throughout the system, as well as the analysis of this data in the proper format, the operations of the blood component collection facilities which utilize this system may be optimized.

In one aspect of the above-identified blood component collection control and information communication system for use with the blood component collection device, the noted data may relate to a specific donor on which a collection procedure is to be performed, process control parameters to be utilized for the collection procedure to be performed on the identified donor, and prior collection procedures which the identified donor has undergone. This data may then be utilized to generate at least one of the process control parameters for the collection procedure to be performed on the identified donor. Once all process control parameters are transferred to the blood collection device via the first and/or second station, the designated collection procedure may be performed.

Data which may be utilized in the optimization of the operation of a given blood component collection facility includes the foregoing, and particularly data relating to collection procedures which have been completed on the noted system. For instance, this data may be recorded, manipulated, and displayed (e.g., on a screen, through a hard copy report) to provide an indication of: 1) the types of collection procedures performed on one or more donors and/or yields associated therewith (i.e., the number of the predetermined type of blood component collected from a given donor) over a specified time period, including on a donor specific basis, a collection procedure specific basis, and/or blood component type specific basis; 2) the net inventory of the quantity of one or more of the various types of blood components over a specified time period; and 3) the quantity of one or more types of blood components collected from one or more donors over a specified time period, including on a blood component type specific basis and/or on a donor basis specific basis.

BRIEF DESCRIPTION OF THE DRAWINGS

FIG. 3 is a schematic representation of one embodiment of a blood component separation assembly which utilizes a single needle configuration and which may be incorporated into the blood component collection system of FIG. 1;

FIG. 4b is a top view of the channel of FIG. 4a;

FIG. 6 is a flow chart of one optimization model for deriving at least one optimal process parameter from a desired blood component yield or from a total procedure time in accordance with principles of the present invention;

FIGS. 9A-G present an example of a donor/patient file report, FIG. 9A being a first portion of the donor/patient file report, FIG. 9B being a second portion of the donor/patient file report, FIG. 9C being a third portion of the donor/patient file report, FIG. 9D being a fourth portion of the donor/patient file report, FIG. 9E being a fifth portion of the donor/patient file report, FIG. 9F being a sixth portion of the donor/patient file report, and FIG. 9G being a seventh portion of the donor/patient file report;

FIGS. 10A-B present an example of a donor/patient vitals report, FIG. 10A being a first portion of the donor/patient vitals report and FIG. 10B being a second portion of the donor/patient vitals report;

FIGS. 11A-B present an example of a procedure summary report, FIG. 11A being a first portion of the procedure summary report and FIG. 11B being a second portion of the procedure summary report;

FIG. 12 is an example of a donor product report;

FIGS. 13A-B present an example of a procedure machine report, FIG. 13A being a first portion of the procedure machine report and FIG. 13B being a second portion of the procedure machine report;

FIGS. 14A-D present an example of a run data report, FIG. 14A being a first portion of the run data report, FIG. 14B being a second portion of the run data report, FIG. 14C being a third portion of the run data report, and FIG. 14D being a fourth portion of the run data report;

FIGS. 15A-D present an example of a donor/patient procedure report, FIG. 15A being a first portion of the donor/patient procedure report, FIG. 15B being a second portion of the donor/patient procedure report, FIG. 15C being a third portion of the donor/patient procedure report, and FIG. 15D being a fourth portion of the donor/patient procedure report;

FIG. 16 is an example of a patient history report;

FIGS. 17A-C present an example of a blood component collection facility production report, FIG. 17A being a first portion of the blood component collection facility production report, FIG. 17B being a second portion of the blood component collection facility production report, and FIG. 17C being a third portion of the blood component collection facility production report;

FIG. 18 is an example of a blood component collection facility staff report;

FIG. 19 is an example of a blood component collection facility statistics report;

FIGS. 20A-B present an example of a donor/patient list, FIG. 20A being a first portion of the donor/patient list and FIG. 20B being a second portion of the donor/patient list;

FIGS. 21A-C present an example of a donor search report, FIG. 21A being a first portion of the donor search report, FIG. 21B being a second portion of the donor search report, and FIG. 21C being a third portion of the donor search report;

DETAILED DESCRIPTION

The present invention will be described with reference to the accompanying drawings which assist in illustrating the pertinent features thereof. Generally, the present invention relates to a blood component collection system which separates, removes, and collects at least one type of blood component (e.g., platelets, red blood cells, white blood cells, plasma) from a source of whole blood (e.g., a donor). More particularly, the present invention is directed to "optimizing" one or more aspects of the operation of blood banks/centers and the like. For instance, "optimization" may be through utilization of a collection procedure derived from a typically site-configured/operator-input goal(s) and the "maximization" of at least one process control parameter. This type of derivation is referred to herein as an "optimization process" and the derived process control parameters are referred to herein as "optimal values."

Figure 1:
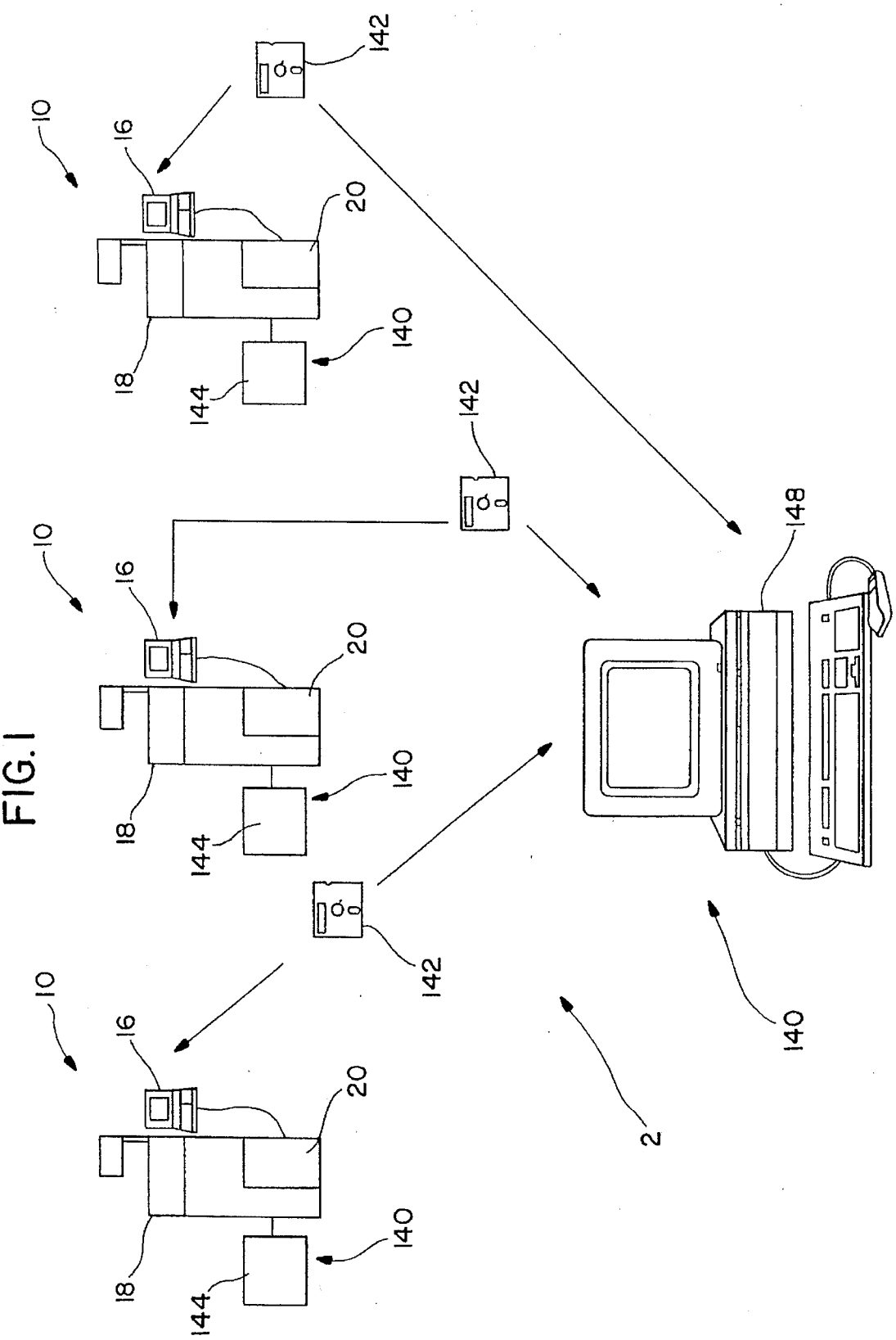
FIG. 1 is a schematic representation of a blood component collection system in accordance with principles of the present invention.

Referring to FIG. 1, the present invention is embodied within the blood component collection system 2 which would typically be implemented at a blood bank/center (not shown). The system 2 includes an optimization assembly 140 (e.g., appropriate microprocessor(s) such as an IBM compatible PC and software) and at least one blood component collection assembly 10 (three shown) which each includes a blood component collection device 18 as an integral part thereof. As will be discussed below, the optimization assembly 140 (or at least a portion thereof) and associated blood component collection assemblies 10 are preferably appropriately interfaced but may be completely separate as well. That is, optimization procedures in accordance with principles of the present invention are not limited to being performed at any particular location.

Generally, the optimization assembly 140 includes a central input station 148 (e.g., an appropriate microprocessor such as an IBM compatible PC and attendant software) for inputting and maintaining donor-related data, and also typically for preparing an initial procedure order (the process control parameters derived from the donor-related data and other considerations) for a given donor. These procedures may also be performed at the appropriate operator interface module 16 as well such that a central input station 148 is not required. However, where a central input station 148 is used, this donor-related data and/or initial procedure order is transferred to one of the operator interface modules 16 (e.g., an appropriate microprocessor such as an IBM compatible microprocessor and interfaced with the device 18 via an RS232 or other lab specific interface, including the Digital Equipment Corp. PCP 30, which is also known as the DEC pc 325SL and which utilizes a 386 processor) which are located at each blood component collection device 18 and which as noted preferably interfaces with an optimizer module 144 (part of the optimizing assembly 140) for providing the operator with one or more optimization options. These optimization options provide a different set of process control parameters than the initial procedure order based upon one or more specified conditions/goals (e.g., input blood component yield, input procedure time) and a particular derivation for the process control parameters. If an optimization option is selected the procedure order is modified to reflect the results of the optimization, the collection procedure is initialized/reinitialized (i.e., the collection procedure would be reinitialized in the case of an optimization which is performed after the collection procedure has been initiated and such is referenced to as a downstream optimization) with the results of the optimization, and the collection procedure is thereafter performed with the blood component collection device 18.

Figure 2:
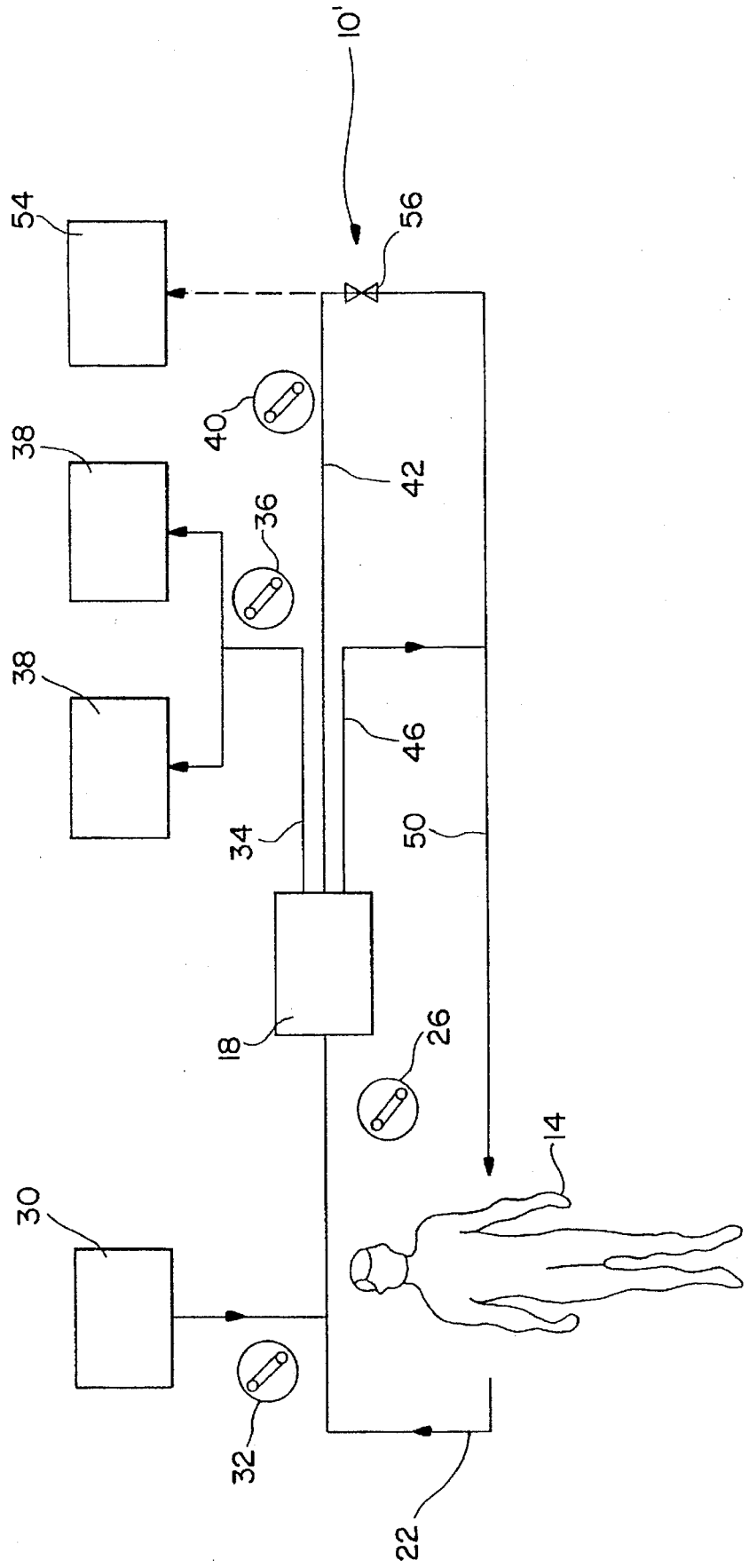
FIG. 2 is a schematic representation of one embodiment of a blood component separation assembly which utilizes a dual needle configuration and which may be incorporated into the blood component collection system of FIG. 1.

Various embodiments of blood component collection assemblies may incorporate principles of the present invention. However, as noted above on-line techniques have been determined to be quite effective and thus the present invention is being described with reference to such techniques. One embodiment of an on-line technique and attendant apparatus which may be incorporated into the blood component collection system 2 of FIG. 1 is illustrated in FIG. 2. The blood component collection assembly 10' utilizes an on-line technique in that a donor 14 (e.g., the whole blood source) is directly integrated with the system 10' by fluid interconnection with the blood component collection device 18. This particular on-line technique is more particularly referred to as a dual needle configuration since there are two fluid interconnections between the donor 14 and the blood component collection device 18.

The donor 14 is fluidly connected to the blood component collection device 18 by an inlet line 22 and appropriate needle assembly (not shown). Whole blood from the donor 14 is thus continuously provided to the blood component collection device 18 through the inlet line 22 for separation of the desired blood component(s) therefrom, utilizing an inlet pump 26 (e.g., a peristaltic pump) to maintain this flow if desired/required. Prior to the blood of the donor 14 entering the blood component collection device 18, anticoagulant from an anticoagulant ("AC") container 30 may be provided to the whole blood, utilizing an AC pump 32 (e.g., a peristaltic pump) to maintain this particular flow if desired/required. Consequently, the inlet flow to the blood component collection device 18 typically includes both a flow of whole blood from the donor 14 and a flow of anticoagulant from the AC container 30.

The blood component collection device 18 separates the whole blood provided on line by the donor 14 into three primary constituents, namely platelets, a combination of red and white blood cells ("RBC/WBC"), and plasma. Although each of these three blood components may be collected using the device 18, the description herein is primarily directed to a platelet collection procedure with an optional plasma collection option. As such, the platelets collected from the blood component device 18 are directed through a platelet collect line(s) 34 to one or more platelet collect bags 38 via a collect pump 36. The plasma and RBC/WBC are provided back to the donor 14 through a plasma line 42 and RBC/WBC line 46, respectively, both of which are interconnected with a second needle assembly (not shown) on the donor 14 via a donor return line 50. The plasma line 42 includes a plasma pump 40 (e.g., a peristaltic pump) to maintain the flow of plasma if desired/required. Although plasma may be provided back to the donor 14 in the above manner, it may be desirable to collect the separated plasma in some cases. In this regard, a plasma collect bag 54 may be provided and interconnected with the plasma line 42 (interconnection shown in phantom). In this case, appropriate valving 56 may be incorporated in the plasma line 42.

The blood component separation assembly 10" of FIG. 3 is similar to that of the dual needle configuration of FIG. 2 except that a single needle assembly (not shown) integrates the donor 14 within the blood component collection assembly 10". Consequently, similar components are similarly identified where appropriate. With regard to the single needle configuration of FIG. 3, whole blood of the donor 14 initially flows through a donor access line 62 and into an inlet line 66 which is fluidly connected with the blood component collection device 18 such that the platelets are separated and collected in the above-described manner. The plasma and RBC from the blood component collection device 18 flow through the plasma and RBC/WBC lines 42, 46, respectively, both of which are fluidly interconnected with a return flow controller 74. As above, however, the plasma may alternatively be directed to a plasma collect bag 54. In the event that plasma is not collected, the RBC/WBC and plasma are provided back to the donor 14 through the return flow controller 74 via a donor return line 70 which is interconnected with the donor access line 62. As can be appreciated, since only a single line is directly connected to the donor 14, namely the donor access line 62, blood is either being removed from or provided back to the donor 14 such that the procedure is effectively two-step versus continuous in relation to the donor 14.

Figure 4A:
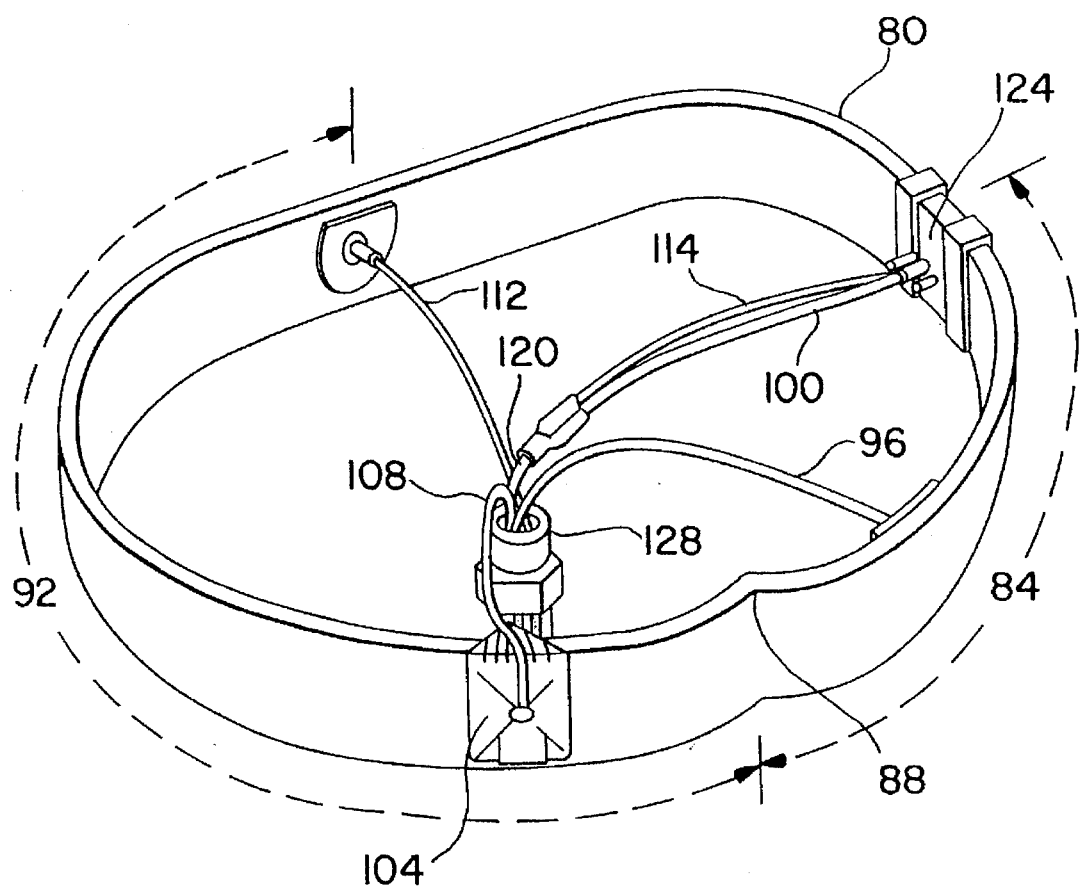
FIG. 4a is a perspective view of one type of a disposable processing channel used in the blood component collection device of FIGS. 2 and 3.
Figure 4B:
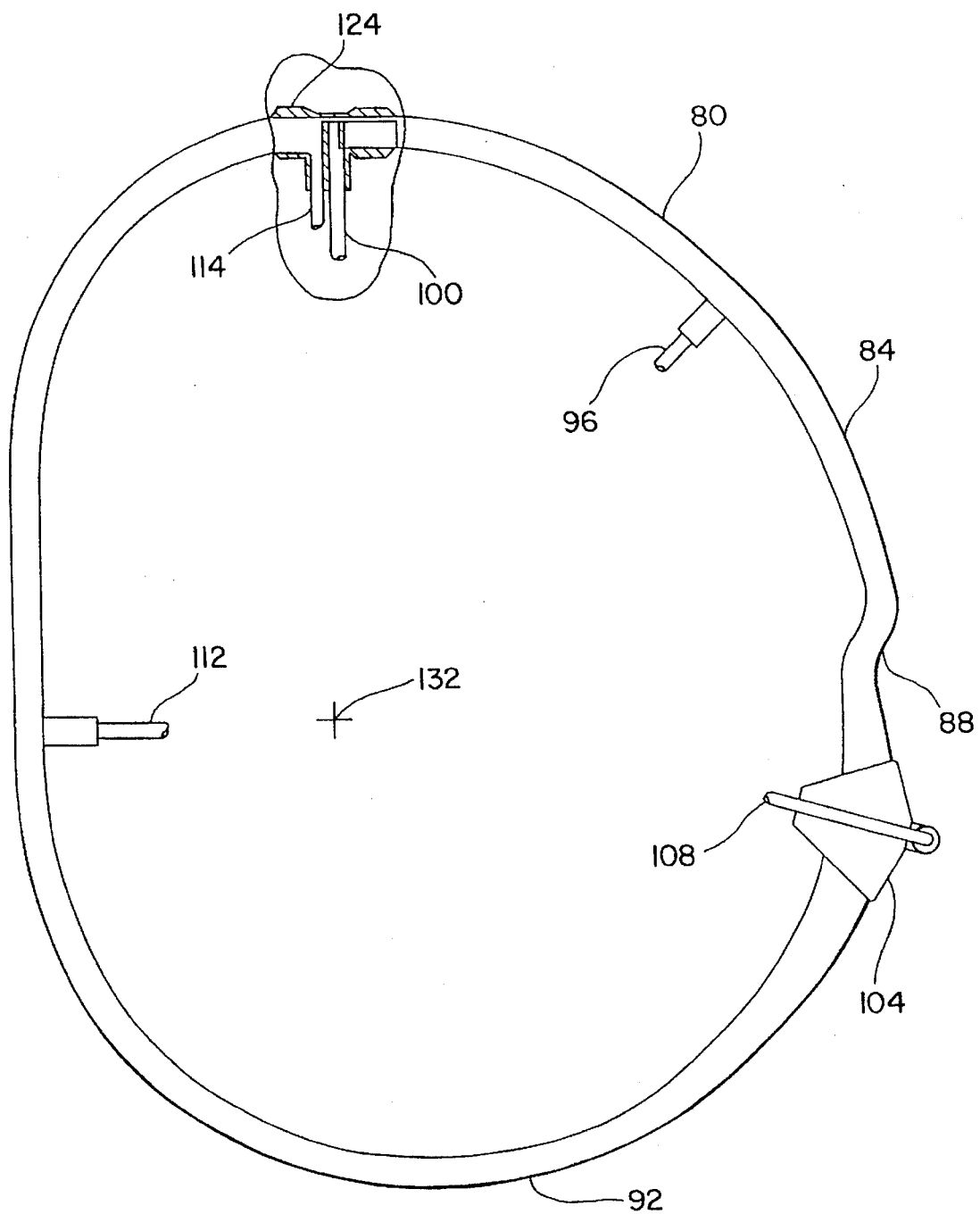

The blood component collection device 18 used in the blood component collection assembly 10 is more particularly illustrated in FIGS. 4A–B. This device 18 is the subject of U.S. Pat. No. 4,387,848 to Kellog et al., entitled "CENTRIFUGE ASSEMBLY", issued Jun. 14, 1983, and the disclosure of which is incorporated by reference in its entirety herein. This device 18 is also commercially available from the assignee of the present application as such is incorporated in COBE Spectra™.

Referring to FIGS. 4A–B, the blood component collection device 18 utilizes a processing channel 80 to provide the desired disposable extracorporeal circuit. The channel 80 is positioned within a groove formed directly or indirectly in a centrifuge rotor (not shown) (e.g., a separate filler may receive the channel 80 and be attached to the centrifuge rotor), and is illustrated in the shape which it assumes during processing (i.e., during flow of blood therethrough). All subsequent references herein to the structural and operational characteristics of the blood component collection device 18 will be to the processing channel 80 in the illustrated condition.

The processing channel 80 generally includes a first stage 84 for collectively separating red blood cells ("RBC") and white blood cells ("WBC") from platelet-rich plasma, a second stage 92 for thereafter separating platelets from the platelet-rich plasma, a transition portion 88 defining a separation between the first stage 84 and second stage 92, and a control chamber 124 for maintaining a proper interface between the first stage 84 and second stage 92, namely the position of the interface between the RBC/WBC and platelet-rich plasma within the transition portion 88.

The first stage 84 extends from one end of the control chamber 124 along an arcuate path generally inwardly, toward the axis 132 about which the processing channel 80 rotates via the centrifuge rotor, until terminating at the transition portion 88. Specifically, the end of the first stage 84 adjacent the control chamber 124 is positioned at a greater radial distance from the axis 132 than the end of the first stage 84 adjacent the transition portion 88. An inlet tube 96 is fluidly connected with the first stage 84 between its two ends to introduce whole blood into the processing channel 80 and a RBC/WBC tube 100 is provided in the control chamber 124 for removing the separated RBC/WBC from the channel 80. Both the inlet tube 96 and RBC/WBC tube 100 extend externally of the rotatable device 18 for interconnection with the donor 14 and/or collection bags 38, 54.

As RBC/WBC sediment against the outer wall in the first stage 84 during rotation of the centrifuge rotor they are directed and counterflow toward the RBC/WBC tube 100 for removal from the channel 80 due to the increased centrifugal forces at the RBC/WBC tube 100 in comparison with the transition portion 88. That is, since the first stage 84 extends along an arcuate path generally outwardly away from the axis 132 proceeding from the transition portion 88 to the control chamber 124, the centrifugal force differential along the first stage 84 establishes the described counterflow of 5 the separated RBC/WBC. Moreover, the transition portion 88 also assists in providing for this counterflow since it extends along an arcuate path generally inwardly toward the axis 132 proceeding from the first stage 84 to the second stage 92.

The platelet-rich plasma, which has a lower density than the RBC and WBC, flows beyond the transition portion 88 from the first stage 84 into the second stage 92 for further processing, while the RBC/WBC are directed back toward the RBC/WBC tube 100 in the above-described manner. The second stage 92 initiates at the radially inwardmost part of the transition portion 88 and extends along an arcuate path generally outwardly away from the axis 132 to a platelet collection chamber 104. Platelets are removed from the processing channel 80 at the platelet collection chamber 104 by a platelet tube 108 which interfaces with the outer wall of the processing channel 80 at the platelet collection chamber 104. Thereafter, the second stage 92 extends along an arcuate path generally inwardly toward the axis 132 until terminating at the plasma tube 112. Both the platelet tube 108 and plasma tube 112 extend externally of the rotatable device 18 for interconnection with the platelet collect bag(s) 38 and donor 14/plasma collect bag(s) 54, respectively.

Platelets which do not separate from the plasma in the initial portion of the second stage 92 between the transition portion 88 and platelet collection chamber 104 are separated in the portion of the second stage 92 between the platelet collection chamber 104 and the plasma tube 112. These platelets will flow back towards the platelet collection chamber 104 in the opposite direction of the flow of platelet-rich plasma/platelet-poor plasma through the second stage 92 due to the configuration of this portion of the second stage 92. That is, the platelet collection chamber 104 assumes the radially outwardmost position in the second stage 92 such that all platelets, regardless of where separation occurs in the second stage 92, flow towards the platelet collection chamber 104 for removal from the channel 80.

Platelet-poor plasma exits the second stage 92 and flows out through the plasma tube 112 which interfaces with the inner wall of the processing channel 80 and/or continues to flow through the remaining portion of the processing channel 80 to the control chamber 124. Plasma which flows to the control chamber 124 exits the channel through the control tube 114 which joins with the RBC/WBC tube 100 into a single outlet tube 120. The positionings and diameters of the RBC/WBC tube 100 and control tube 114 and the joinder of such into the common outlet tube 120 regulate the position of the RBC/WBC-platelet-rich plasma interface within the transition portion 88 using conservation of mass principles.

The blood component collection device 18 includes a prediction model 20 (appropriately interfaced with the operator input module 16 as shown in FIG. 1 as noted above and which may be used to configure the prediction model 20 and/or to allow operator input of various parameters to be used by the prediction model 20) for predicting a platelet yield before a collection procedure is initiated using a compilation of algorithms. The prediction model 20 may be used by the optimizer assembly 140 which is associated with principles of the present invention and thus will be briefly described herein. Notwithstanding the following discussion of the specifics of the prediction model 20, those skilled in the art will appreciate that the prediction model 20 is associated with the functional and operational characteristics of the blood component device 18 described herein. Therefore, the algorithms used in the prediction model 20 could and likely would vary in the case of other blood component collection devices which may be used by the present invention. Moreover, different algorithms could of course be used even for the prediction model 20. Furthermore, the algorithms are specific to platelet collection and therefore may and likely would change if used in relation to other blood component types such as red blood cells.

The prediction model 20 is typically configured by the site (e.g., the blood bank/center) for a particular blood component collection procedure (e.g., single or dual needle) used by the site and will be presented with regard to the dual needle procedure of FIG. 2 and in relation to a platelet-collecting procedure. In this regard, an AC infusion rate (i.e., the rate at which anticoagulant is provided to the donor 14 per the blood volume of the donor 14) and the AC ratio (i.e., the collective flow of AC and blood through the inlet line 22 in relation to the flow of AC through the line 22) must be specified (through configuration or modified input as will be discussed below). Moreover, in the event that plasma is to be collected into the plasma collect bag 54 in the collection procedure, the maximum amount of plasma which should be collected considering the medical and physical characteristics of the donor 14 must also be provided.

There are two alternatives for establishing the plasma volume limit. The first alternative relating to the plasma volume limit is to provide a weight cutoff (e.g., 0–500 pounds), associated with the weight of the donor 14 which is input as will be discussed below. In this regard, a plasma volume upper limit (e.g., 10–1500 ml.) may be established for a weight of a donor 14 in excess of this cutoff, and a plasma volume lower limit (e.g., 10–1500 ml.) may be established for a weight of such donor 14 which is less than this cutoff. For instance, if the weight cutoff is 175 pounds, the plasma volume upper limit can be 600 ml. for a donor 14 weight greater than or equal to 175 pounds, and the plasma volume lower limit can be 500 ml. for a donor 14 weight less than 175 pounds.

The second alternative for a plasma volume limit is to configure the prediction model 20 such that the plasma volume limit is expressed as a percentage of the total blood volume of the donor 14 which is calculated pursuant to Eq. 10 below. For instance, the plasma volume limit may be established as 1–15% of the total blood volume of the donor 14, and is preferably established as about 12% of such volume.

Further information is required by the prediction model 20 prior to performing its yield prediction function. For instance, the total procedure time is typically input by the operator or preconfigured by the user (e.g., the blood bank/ center). When configured the procedure time is typically 100 minutes. Moreover, the total procedure time is affected by whether a stepdown option is utilized for the blood component collection device 18 so as to enhance separation of the various blood components. When this stepdown option is selected, the angular velocity of the blood component collection device 18 is incrementally reduced during the platelet-collection procedure. For instance, the stepdown option could provide for angular velocities for the device 18 of 2400, 2200, and 2000 RPM, each of which would be for a specified duration.

Based upon the foregoing, the configuration of the prediction model 20 in relation to the blood component separation assembly 10' and associated protocol in effect standardizes site protocol for purposes of "normal" operations. However, for a particular donor 14 it may be desirable to alter the "configuration" for one processing run. Consequently, the prediction model 20 utilizes a procedure in which certain parameters utilized in the following equations may be adjusted on a one-at-a-time basis. Such is referred to as modified input data and the associated parameters are procedure time (e.g., 10–999 minutes), inlet flow rate to the device 18 (e.g., 0–150 ml/min. for the FIG. 2 assembly and 0–50 ml/min. for the FIG. 2 assembly), AC ratio option as discussed above (3–50), the desired platelet collect volume (e.g., 10–9999 ml.), the desired platelet collect concentration (e.g., 100–8000×10⁶/ml.), and the desired source plasma volume to be collected (e.g., 0–9999 ml.). Moreover, other parameters such as AC infusion rate (0.8–1.1), stepdown option (yes or no), needle option (single or double), and high flow option (yes or no) may also be entered as modified input data by an operator.

Having configured the prediction model 20 in the above-described manner, the following additional information is provided and is utilized in the various calculations of Equations 1–22 presented below: (1) needle option, namely whether the procedure is dual needle (FIG. 2) or single needle (FIG. 3); (2) run identification number for purposes of associating the data/output generated by the various equations with a particular donor 14 and processing run; (3) the sex of the donor 14; (4) the height of the donor 14; (5) the weight of the donor 14; (6) the total blood volume as calculated in Eq. 10 below; (7) the hematocrit of the donor 14, either based upon an initial estimation and thereafter updated based upon analysis of the donor's 14 blood sample (e.g., by a cell counter) or input directly from such an analysis; (8) the platelet precount, either based upon an initial estimation and thereafter updated based upon analysis of the donor's 14 blood sample (e.g., cell counter) or input directly from such an analysis; and (9) whether plasma collection is desired in conjunction with the platelet collection.

Based upon the above initial configuration and subsequent data input (except when entered as modified input data), the following output is generated by the prediction model 20: (1) platelet yield; (2) inlet flow rate; (3) AC ratio; (4) procedure time; (5) platelet collect volume; (6) platelet collect concentration; (7) source plasma volume; (8) AC in the platelet and plasma collect bags 38, 54; (9) platelet postcount; (10) AC infusion rate; and (11) output approval. This information is utilized at least in part in the following equations to generate, inter alia, the predicted platelet yield value of the collected platelets for the case of the dual needle procedure of FIG. 2 and also for the case of the single needle procedure of FIG. 3. The differences between those procedures with regard to the prediction model 20 are identified herein. As will be appreciated, some of the equations are utilized in the calculation of the predicted platelet yield, whereas other equations are used to generate additional information for output and informational purposes. The variables or parameters and the units associated therewith of the equations are presented after the equations in the Variables Index.

Platelet Yield:

$$Y = 1 \times 10^6 C_{PR} V_B F_Y [1 - exp[-E_c(f_{BP} - 0.12)]] \quad \text{(Eq. 1)}$$

where:

$$f_{BP} = (Q_{IN} t_E + 50)(1 - 1/R)/V_B \quad \text{(Eq. 2)}$$

and where:

$$Q_{IN} = RQ_{AC} = 0.001 \, I \, V_B PR \leq 150 \quad \text{(Eq. 3)}$$

Alternatively, the platelet yield may be expressed as:

$$Y = 1 \times 10^6 C_{PR} V_B F_Y [1 - exp[-E_c(0.001 \, I(R-1)Pt_E + 50(1-1/R)/V_B - 0.12]] \geq 0 \quad \text{(Eq. 4)}$$

Platelet Collection Efficiency:

$$E_c = C_1 - C_2 \, exp \, [9.91(1-1/R)H]Q_{INA} \geq 0 \quad \text{(Eq. 5)}$$

where the constant $C_1$ is defined as follows:

$C_1 = 0.803$–*dual needle, without stepdown*

$C_1 = 0.840$–*dual needle, with stepdown* where the constant $C_2$ is defined as follows:

$C_2 = 4.08 \times 10^{-5}$–*dual needle, without stepdown–dual needle, with stepdown* and where:

$$Q_{INA} = Q_{IN}(t_E/t_P) \quad \text{(Eq. 6)}$$

In Eq. 6, $t_P$ may be provided as configuration data or modified data as provided above, or alternatively may be derived from the solution of Eq. 4 for $t_E$.

Effective Procedure Time:

$$t_E = t_P, Q_{IN} \leq 45 \quad \text{(Eq. 7)}$$
$$= t_P - 500\,(1/45 - 1/Q_{IN}), Q_{IN} > 45$$

Only high-flow protocol is used for $Q_{IN} > 45$.

AC Infusion Rate Constant:

$$I = 1000\,Q_{IN}/(PRV_B) \quad \text{(Eq. 8)}$$

Alternatively to the use of Eq. 8 for the derivation of the AC infusion rate constant I, such may be provided as configuration or modified input data pursuant to the above.

AC Ratio:

Initially, the AC ratio may be provided as configuration or modified input data pursuant to the above. In configuration, it is defined as follows:

$$R = 1 + 2.51/H \quad \text{low} \quad \text{(Eq. 9)}$$
$$= 1.33(1 + 2.51/H) \quad \text{medium}$$
$$= 1.67(1 + 2.51/H) \quad \text{high}$$

Total Blood Volume:

$$V_B = 604 + 0.006012\,L^3 + 14.6\,W\,\text{ml} \quad \text{(male)} \quad \text{(Eq. 10)}$$
$$= 183 + 0.005835\,L^3 + 15.0\,W\,\text{ml} \quad \text{(female)}$$

Plasma Collect Factor:

AC infusion rate control maintains the AC flow to the donor as:

$$Q_{ACD} = 0.001\,I\,V_B \quad \text{(Eq. 11)}$$

where the inlet flow associated with this is:

$$Q_{INO} = RQ_{ACD} = 0.001\,IRV_B \quad \text{(Eq. 12)}$$

$Q_{IN}$ is proportional to the total AC flow, as given by Eq. 3, which includes the AC that flows to the platelet collect bag 38 and the plasma collect bag 54. P (Eq. 13) is the factor by which $Q_{IN}$ is increased by collecting AC, relative to not collecting AC. That is, $$P = Q_{IN}/Q_{INO} = (\text{average } Q_{AC})/Q_{ACD} \quad \text{(Eq. 13)}$$

where:

$$P = 1 + (f_{ACP}/Q_{ACD})[V_C/(t_P - 150/Q_{IN}) + V_{SP}/(t_P - 500/Q_{IN})] \quad \text{(Eq. 14)}$$

and where:

$$f_{ACP} = [(R-1)(1-H)]^{-1} \quad \text{(Eq. 15)}$$

Platelet Collect Volume:

$$V_C = 1 \times 10^{-6}\,Y/[C_B(1 + f_{ACP})] \quad \text{(Eq. 16)}$$

Source Plasma Volume:

The four choices provided are as follows:

$$\left. \begin{array}{l} V_{SP} = 0 \\ = V_{CON} - V_C \\ = f_{SP}V_B - V_C \\ = \text{specified as modified input} \end{array} \right\} \geq 0 \quad \text{(Eq. 17)}$$

where:

$$V_{CON} = V_{CONL}, W < W_C \quad \text{(Eq. 18)}$$
$$= V_{CONH}, W \geq W_C$$

and where:

$$0.01 \leq f_{SP} \leq 0.15 \quad \text{(Eq. 19)}$$

Donor Postcount:

$$C_{PO} = C_{PR}\exp[-E_C(0.001\,I\,(R-1)Pt_E + 50\,(1 - 1/R)/V_B - 0.12)] \quad \text{(Eq. 20)}$$

A warning is given if $C_{PO} < 100$.

Collect Volumes:

$$V_{CB} = V_C(1 + f_{ACP}) \quad \text{(Eq. 21)}$$

$$V_{SPB} = V_{SP}(1 + f_{ACP}) \quad \text{(Eq. 22)}$$

The primary equation to be solved for purposes of the yield prediction by the prediction model 20 is Eq. 4. Consequently, Eqs. 1–3 and 5–22 are ancillary to Eq. 4 although they may be used to calculate other output data and/or information required by Eq. 4. With regard to the manner in which Eqs. 1–22 are solved, all the iteration loops are based on the technique of successive approximation, in which each iteration is a repeat of the previous one, but using updated parameter values calculated in the previous iteration. This process continues until all the convergence criteria are met. The convergence criteria are that, on successive iterations, the variable difference is $\leq 1$ for $V_C$, $\leq 0.2$ for $t_E$, and $\leq 10$ for $C_B$.

As noted above, the foregoing was based upon a dual needle configuration as illustrated in FIG. 2. In the event that a single needle configuration such as that illustrated in FIG. 3 is utilized, the following Eq. 7' is used in place of Eq. 7 and the constants $C_1$ and $C_2$ for Eq. 5 are as follows:

$$C_1 = 0.803$$
$$C_2 = 8.54 \times 10^{-5}$$

$$t_E = t_P, Q_{IN} \leq 20 \quad \text{(Eq. 7')}$$
$$= t_P - 215\,(1/20 - 1/Q_{IN}), Q_{IN} > 20$$

Variables Index

Symbols for Equations:

| | |
|---|---|
| $C_1, C_2$ | = constants in platelet collection efficiency equations |
| $C_B$ | = platelet concentration in collect bag, expressed as $10^3$ platelets, microliter |
| $C_{PO}$ | = donor postcount, expressed as $10^3$ platelets/microliter |
| $C_{PR}$ | = donor precount, expressed as $10^3$ platelets/microliter |
| $E_C$ | = platelet collection efficiency |
| $f_{ACP}$ | = AC expressed as a fraction of pure plasma volume |
| $f_{BP}$ | = fraction of $V_B$ processed in platelet collection procedure |
| $f_{SP}$ | = $V_{CON}$ expressed as a fraction of $V_B$ |
| $F_Y$ | = user-specific (e.g., blood bank/center) yield calibration factor |
| H | = hematocrit of donor or patient |
| I | = AC infusion rate constant |
| L | = donor or patient height, inches |
| P | = plasma collect factor |
| $Q_{AC}$ | = AC flow, ml/min |
| $Q_{ACD}$ | = AC flow infused into donor for platelet |

-continued

Variables Index

Symbols for Equations:

| | | |
|---|---|---|
| | | collection procedures, ml/min |
| $Q_{IN}$ | = | inlet flow, ml/min |
| $Q_{INA}$ | = | average inlet flow for platelet procedures, ml/min |
| $Q_{INO}$ | = | $RQ_{ACD}$ = inlet flow associated with $Q_{ACD}$, ml/min |
| R | = | AC ratio |
| $t_E$ | = | equivalent procedure time, min |
| $t_P$ | = | procedure time, min |
| $V_B$ | = | total blood volume of donor or patient, ml |
| $V_C$ | = | volume of pure plasma in platelet collect bag, ml |
| $V_{CB}$ | = | total volume in platelet collect bag, ml |
| $V_{CON}$ | = | volume constraint for total pure plasma collected, ml |
| $V_{CONH}$ | = | higher value of $V_{CON}$, ml |
| $V_{CONL}$ | = | lower value of $V_{CON}$, ml |
| $V_{SP}$ | = | volume of pure plasma in source plasma bag, ml |
| $V_{SPB}$ | = | total volume in source plasma bag, ml |
| W | = | donor or patient weight, lbs |
| $W_C$ | = | weight constraint associated with $V_{CON}$, lb |
| Y | = | platelet yield, number of platelets. |

In summary the prediction model 20 is able to predict the blood component yield (i.e., the number of the selected blood component type) before the procedure is actually initiated. Yield information may also be provided during and/or after 5 blood component collection procedures, such as through use of an on-line monitoring device such as that disclosed in U.S. Pat. No. 4,810,090 to Boucher et al., entitled "METHOD AND APPARATUS FOR MONITORING BLOOD COMPONENTS", and issued Mar. 7, 1989. U.S. Pat. No. 4,810,090 is incorporated by reference in its entirety herein. Generally, this on-line monitoring device is referred to as a Collect Concentration Monitor ("CCM") and utilizes an optical detector which passes through the flow of platelets out through the platelet collect line. A platelet sensor is appropriately positioned in a portion of the platelet collect line between the device 18 and the platelet collect bag (not shown). The platelet sensor generally includes a central detector, which coincides with the axis in which the light is initially directed through the flow, and annular detectors. These independent detectors are utilized in conjunction with each other to determine the instantaneous concentration of collected platelets passing by the monitoring device. Using this estimated platelet concentration and the flow rate of the platelets being collected and passing through the platelet collect line, the instantaneous rate at which platelets are being collected may be determined. By integration the current platelet yield may thus be determined. At the end of the given platelet harvesting procedure, this determination will thus constitute a monitored yield value.

As noted above, the optimizer assembly 140 associated with principles of the present invention interfaces with or at least provides information to one or more blood component collection assemblies 10 to provide a blood component collection system 2. That is, although there are definite advantages to having an interface between the optimizer assembly 140, particularly the optimizer module 144, and the blood component collection device 18, the optimization procedure may be performed at any location and input into the blood component collection device 18 in any manner. Since the general principles of the blood component collection assembly 10 were described with relation to the collection assemblies 10, 10" which included the blood component collection device 18 and its various features, the optimizer assembly 140 will be described in relation to such assemblies 10', 10". However, it will be appreciated that the fundamental optimization principles of the present invention are not limited to these collection procedures and/or apparatus.

As noted (FIG. 1), the optimization assembly 140 generally includes a central input station 148, as well as an optimizer module 144 for each blood component collection device 18. Initially, it should be noted that the optimizer module 144 may be separate from the internal control of the blood component collection device 18 which is accessible by the operator interface module 16. However, typically the optimizer module 144 will be integrated with this internal control along with the above-described prediction model 20.

Figure 5:
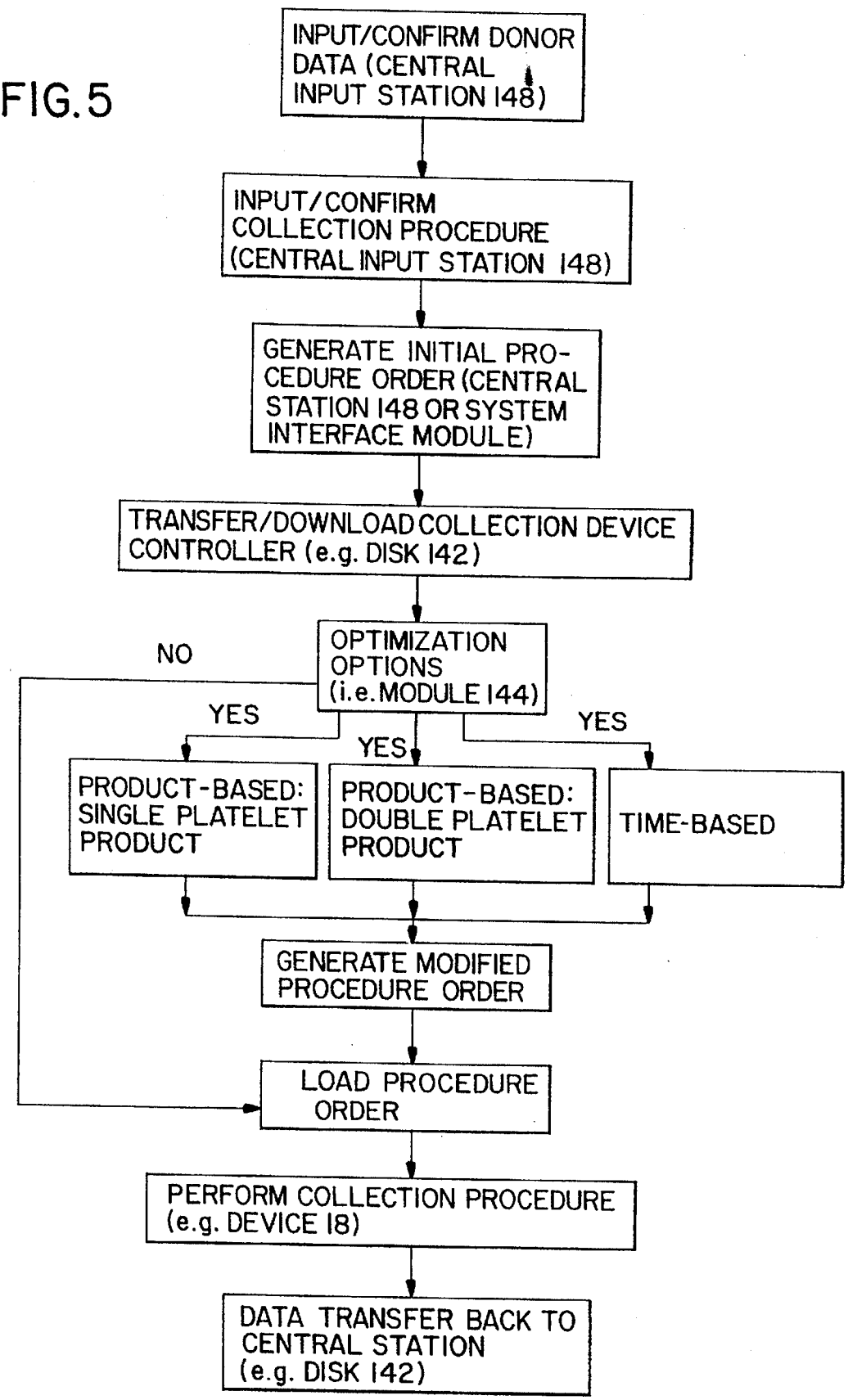
FIG. 5 is a flow chart of a blood component collection procedure utilizing principles of the present invention.

Referring to FIG. 5, the optimizer assembly 140 will be described with regard to a standard procedure. The central input station 148 will typically be used by blood banks/centers as the primary means for donor data input and donor data management. Information relating to a donor such as sex, height, weight, and demographics will be input at the central input station 148. Moreover, information relating to the donor's hematocrit and a blood component precount, both of which may be obtained from a donor blood sample and determined by known techniques such as cell counters, may also be entered at the central input station 148. In addition to donor-related data, the particular type of collection procedure to be used for the donor (e.g., single needle or double needle) may be input/confirmed at the central input station 148. Based upon this information and certain site-standardized conditions (e.g., total procedure time, collection efficiency, AC infusion rate), an initial procedure order is thereafter generated which specifies the various process control parameters associated with the selected collection procedure.

The initial procedure order may be transferred/downloaded onto the internal control of a blood component collection device 18 by a computer disk 142 (FIG. 1) or electronically if a network system is implemented (not shown), through use of the operator interface module 16 if required/desired. When this operator interface module 16 exists, it may of course be used for the initial donor data input and/or to generate the initial procedure order and thereby alleviate the need for a central input station 148. However, it may be more efficient to use the central input station 148. Although this initial procedure order may be used in the collection process, the initial procedure order may be optimized in accordance with principles of the present invention to obtain one or more optimal values for the process control parameters. As noted, this optimization process may be utilized before the collection procedure is actually initiated, but may also be initiated during a given collection procedure and such is referred to as downstream optimization.

Figure 7:
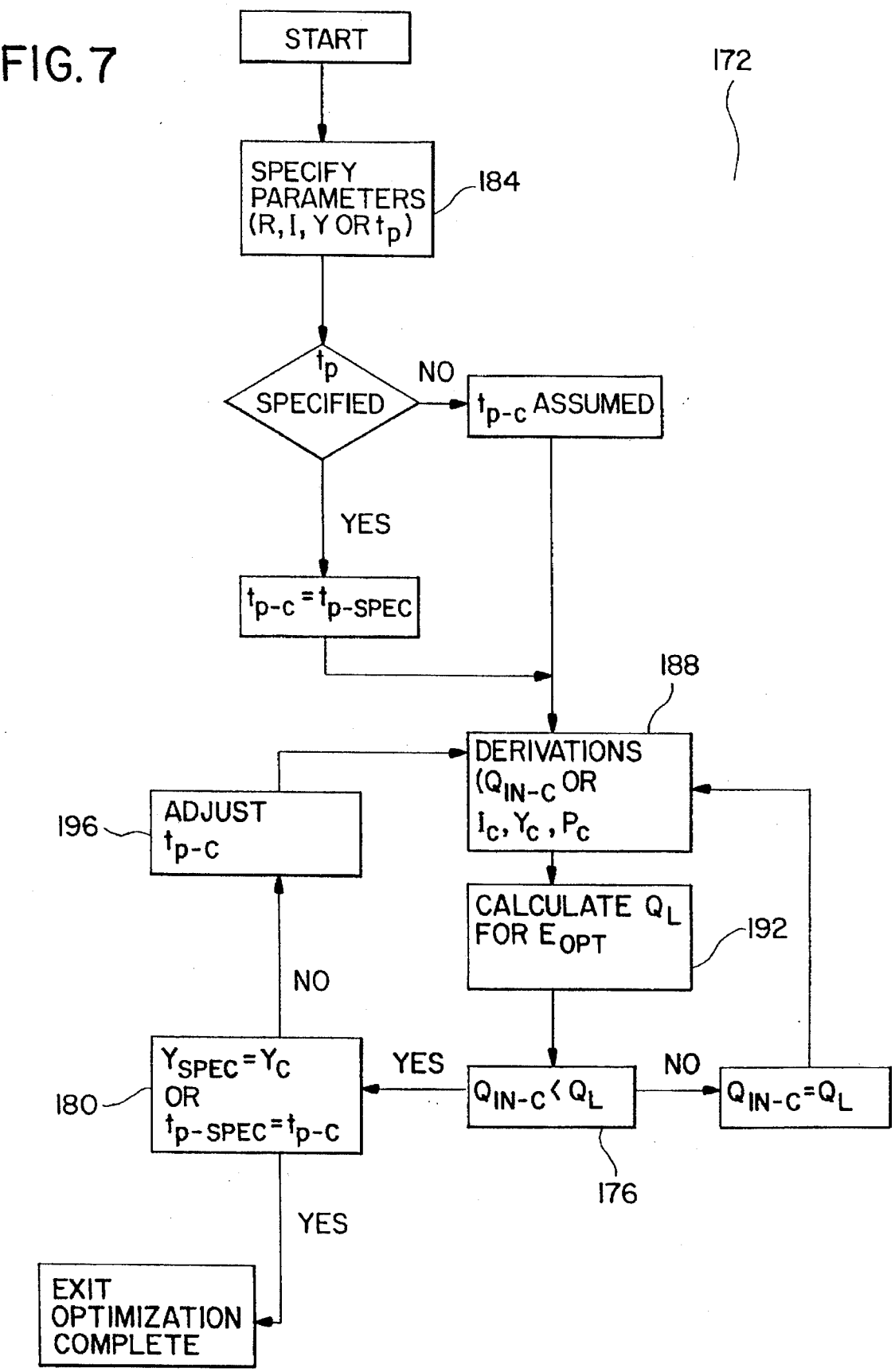
FIG. 7 is a flow chart of one optimization model for deriving at least one optimal process parameter from a desired blood component yield or from a total procedure time in accordance with principles of the present invention.

With regard to the various optimization options, process control parameters may be derived for a product-based optimization. More particularly, the optimizer assembly 140 and specifically the optimizer module 144 derives process control parameters for achieving a predetermined yield of blood components through a maximization of at least one process parameter as will be discussed below in relation to the optimization models 152 (FIG. 6), 172 (FIG. 7). As noted above, in the United States a single platelet product (SPP) is $3\times10^{11}$ platelets and a double platelet product (DPP) is $6\times10^{11}$ platelets. Consequently, the optimizer module 144 may be configured to provide a number of product-based optimizations such as SPP and DPP. Although the exact values for a current U.S. SPP and DPP could be configured into the optimizer module 144, in order to increase the probability that the actual yield will equal or exceed the yield requirements for a current U.S. SPP or a DPP, the site may configure a SPP to be $3.5 \times 10^{11}$ platelets and a DPP to be $7.0 \times 10^{11}$ platelets (e.g., to effectively provide a given confidence level that the specified yield will actually be met).

The optimizer module 144 may also be configured to provide a time-based optimization. That is, for a given amount of time which a donor is available, the optimizer module 144 will derive those process parameters which allow for the collection of a "maximum" amount of platelets in this time period in relation to a maximization of at least one of the process control parameters.

Once the optimization is complete, the values for the various process control parameters generated thereby, as well any ancillary/previously specified values, are downloaded from the operator interface module 16 to the internal control of the blood collection device 18 such that the collection procedure may be initiated or reinitiated (downstream optimization) as the case may be in accordance with these values. Since the operator interface module 16 interfaces with its associated blood component collection device 18, it is able to monitor the performance of the collection procedure and/or record data throughout the procedure and display various types of data to the operator which may be of assistance in conducting the procedure. Once the procedure is completed, certain data is transferrable (via the disk 142 or electronically as noted) from the operator interface module 16 back to the central input station 148 for further use with regard to the particular donor. Various types of data in various formats discussed in more detail below may be displayed to an operator at the central input station 148. In addition, this information as well as the initial input may be used to generate various types of reports as will be discussed in more detail below from the central input station 148. Generally, these types of reports may assist in the management of the blood bank/center (e.g., individual run, donor/patient, summary reports). Moreover, this information may be used in the derivation of subsequent procedure orders for the particular donor (i.e., a "standardized" procedure order for a specific donor). For instance, in the event that a certain AC infusion rate was used in the collection procedure which had certain effects on the donor, this may be recorded in the central input station 148 such that a lower AC infusion rate would be suggested/required for subsequent donations by the donor.

Figure 6:
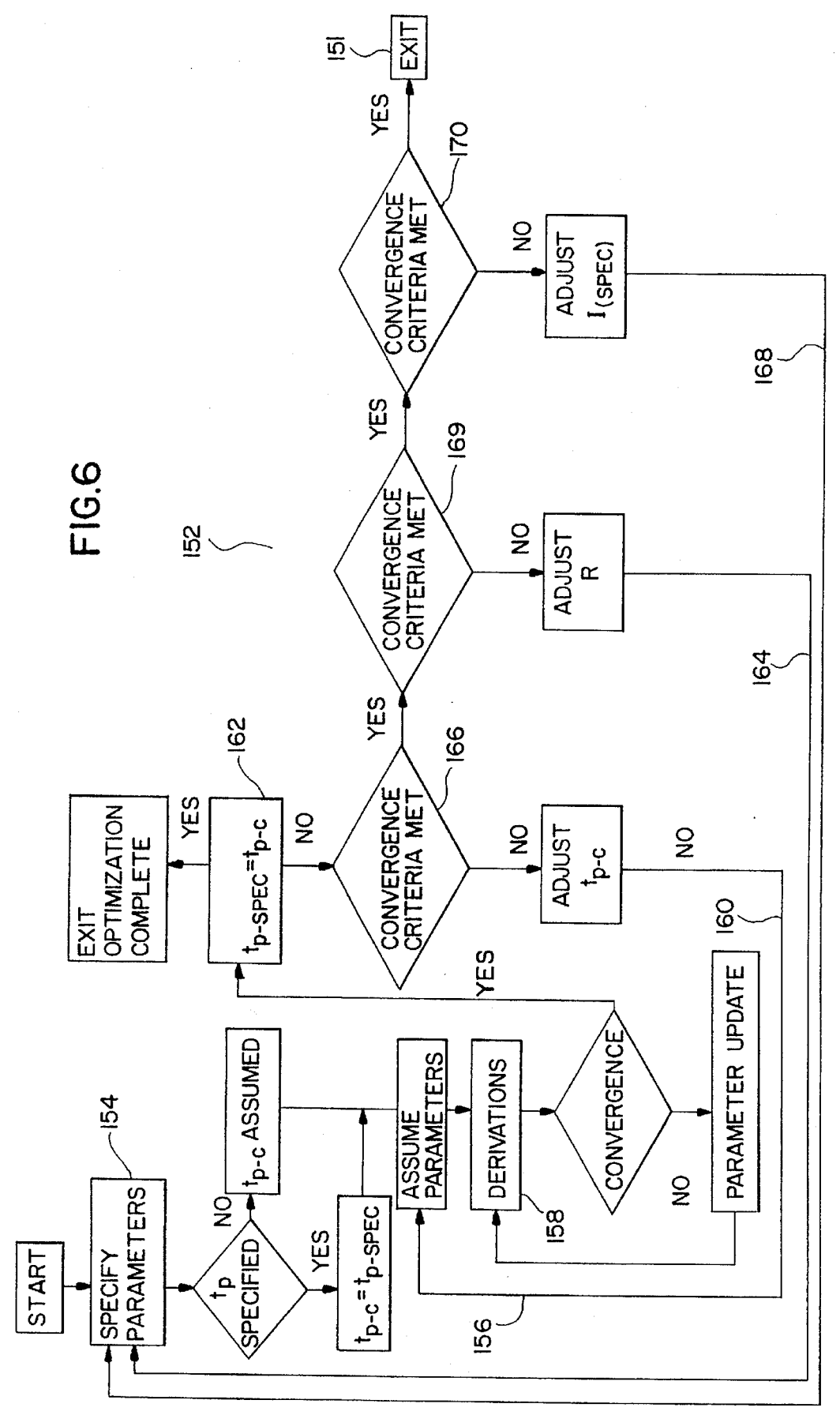

One model which may be incorporated into the optimization module 144 is illustrated in FIG. 6 and will be described with regard to platelet collections in accordance with the dual needle configuration of FIG. 2, although the module 144 may be used with a variety of other collection procedures and including the single needle configuration of FIG. 3, as well as with various other blood components. Initially, it should be noted that all references in FIG. 6 to "derivations" are actually provided by the prediction model 20 discussed above such that there is either an appropriate interface between the prediction model 20 and optimizer module 144 or the optimization module 144 actually includes the prediction model 20. Moreover, as noted the prediction model 20 is specific to the blood component collection device 18 and to platelet collections. Therefore, if other devices are used the associated prediction model would also likely change as noted. Moreover, the associated prediction model may also vary in the case where different blood components such as red blood cells are to be collected.

The optimizer model 152 of FIG. 6 may be used for both product-based and time-based optimizations. Initially, the optimizer model 152 will be described with regard to a product-based optimization. That is, the fundamental premise of the optimization is to achieve a predetermined platelet (or other blood component type) yield (or within a yield range), preferably in the minimum amount of time.

The optimizer model 152 of FIG. 6 is comprised of four iterative loops. Generally, the first loop 156 is a derivation of an inlet flow ($Q_{IN}$) associated with a specified AC infusion rate ($I_{SPEC}$) which is typically set at a maximum value for purposes of the present invention and which is entered at the input station 154. This derivation is thereafter performed by the processing station 158 and includes the solution of Eqs. 4, 8, 14, and 16 and/or equations ancillary thereto by the prediction model 20 as discussed above.

There are of course various convergence criterion/criteria which may be incorporated into the first loop 156. For instance, convergence may be based upon the current inlet flow ($Q_{IN-C}$) in the first loop 156 through use of a binary search technique. In this case, in solving the noted equations at the processing station 158 certain parameters remain fixed in the iterative derivation of the inlet flow ($Q_{IN}$) which achieves the specified AC infusion rate ($I_{SPEC}$) and these parameters are also specified at input station 154. These include the total blood volume ($V_B$) which can be calculated using Eq. 10 since the donor's height, weight, and sex are entered at the central input station 148, and the AC ratio (R), which can be calculated using Eq. 9 since the donor's hematocrit (H) has been determined, or may be specified at some value. Moreover, the total procedure time ($t_P$) remains fixed in each iterative derivation of the inlet flow ($Q_{IN}$) associated with the specified AC infusion rate ($I_{SPEC}$) in the first loop 156. However, since the total procedure time ($t_P$) is not known in the case of a product-based optimization and thus cannot be specified at the input station 154, a current total procedure time ($t_{P-C}$) initially will be assumed (e.g., this assumption is configured in the optimizer model 152 and since a range of total procedure times is provided in the prediction model 20 as noted above, the mean total procedure time ($t_P$) is typically configured into this portion of the optimizer model 152 as the initial current total procedure time ($t_{P-C}$)). The "current" designation is used for the total procedure time in this case since the optimizer model 152 provides for an adjustment of the total procedure time after each iterative determination of the inlet flow ($Q_{IN}$) which provides the specified AC infusion rate ($I_{SPEC}$) in the second loop 160 in order to achieve the desired yield (Y) if required in the case of a product-based optimization as will be discussed in more detail below.

Generally, the inlet flow-based binary search technique convergence may be provided by assuming a current value for the inlet flow ($Q_{IN-C}$), calculating a current plasma collect factor ($P_C$) using the current total procedure time ($t_{P-C}$), calculating a current AC infusion rate ($I_C$) using the current inlet flow ($Q_{IN-C}$) and current plasma collect factor ($P_C$), and adjusting the current inlet flow ($Q_{IN-C}$) (at the parameter update in the first loop 156) in accordance with the selected binary search technique until there is a predetermined convergence between the two most recent values for the current inlet flow ($Q_{IN-C}$) (i.e., wherein the difference between the two most recent values of $Q_{IN-C}$ is less than some predetermined amount which means that the convergence criterion is met). In the case of a binary search technique, there will always be convergence (i.e., the convergence criterion will always be met) such that the optimizer model 152 will always exit the first loop 156 and enter the second loop 160.

As an alternative to the noted inlet flow-based convergence criterion/criteria and the noted binary search technique, another possibility is to base convergence on the specified AC infusion rate ($I_{SPEC}$) and use an iterative derivation to determine the desired inlet flow ($Q_{IN}$). In this case, the first loop 156 is used to once again iteratively derive the inlet flow ($Q_{IN}$) which provides the specified AC infusion rate ($I_{SPEC}$) at the processing station 158 from certain specified parameters. That is, the first loop 156 is still a maximization of the inlet flow ($Q_{IN}$) based upon the specified AC infusion rate ($I_{SPEC}$) which should be associated with the donor 14. This is again primarily through the solution of Eqs. 4, 8, 14, and 16 and/or equations ancillary thereto by the prediction model 20 discussed above.

For purposes of solving the above-identified equations in relation to the infusion rate-based convergence criterion, certain parameters remain fixed in the iterative derivation of the inlet flow ($Q_{IN}$) which achieves the specified AC infusion rate ($I_{SPEC}$) in the first loop 156 and these parameters are also specified at the input station 154. These include the specified AC infusion rate ($I_{SPEC}$) which is known and which is typically a maximum value for the donor 14, the total blood volume ($V_B$) which can be calculated using Eq. 10 since the donor's 14 height, weight, and sex are entered in the central input station 148, and the AC ratio (R) which can be calculated using Eq. 9 since the donor's 14 hematocrit (H) has been determined and input in the central input station 148, or may be entered as modified input data. Moreover, the total procedure time ($t_P$) remains fixed in each iterative derivation of the inlet flow ($Q_{IN}$) associated with the specified AC infusion rate ($I_{SPEC}$). However, once again the total procedure time ($t_P$) is not known in the case of a product-based optimization and thus cannot be specified at the input station 154. Therefore, a current total procedure time ($t_{P-C}$) initially will be assumed (e.g., this assumption is configured in the optimizer model 152, and since a range of total procedure times is provided in the prediction model 20 as noted above, the mean total procedure time ($t_P$) is typically configured into the first loop 156 of the optimizer model 152). The "current" designation for the total procedure time is used for the above-identified reasons relating to the adjustment of the total procedure time in the second loop 160 if required to attain the desired yield (Y).

The solution of Eqs. 4, 8, 14, and 16 also requires that certain values be assumed for certain of the remaining parameters with still other parameters being derived from this assumption. In this case, an iterative procedure is used and updated/current values are used in the next iterative calculation(s). All parameters which change on each iteration of the first loop 156 are identified herein with a "c" subscript to designate that the most current value is to be used. Although the derivation of that inlet flow ($Q_{IN}$) which provides the specified AC infusion rate ($I_{SPEC}$) may be accomplished in a variety of manners via Eqs. 4, 8, 14, and 16, one way is to assume a current value for the plasma collect factor ($P_C$), then calculate the current inlet flow ($Q_{IN-C}$) using the specified AC infusion rate ($I_{SPEC}$), then calculate the current yield ($Y_C$), then calculate the current plasma collection factor ($P_C$) using the current yield ($Y_C$), and repeat this procedure with the current values until there has been acceptable convergence on the current inlet flow ($Q_{IN-C}$) in relation to the specified AC infusion rate ($I_{SPEC}$) (e.g., when the particular convergence criterion/criteria is met/established). When there is acceptable infusion rate-based convergence, the optimizer model 152 exits the first loop 156 and enters the second loop 160. In order to offer protection for cases when there is no such convergence, a maximum number of iterations for the first loop 156 may be specified (not shown).

The second loop 160 of the optimizer model 152 is a total procedure time ($t_P$) iteration. That is, the second loop 160 is an iterative adjustment of the current total procedure time ($t_{P-C}$). Initially, in the second loop 160 and in the case of a product-based optimization the model 152 will never exit at the first comparator 162 since a total procedure time ($t_P$) is not specified at the input station 154. Consequently, the optimizer model 152 proceeds to the second comparator 166 where convergence criteria (i.e., more than one check) is made. One convergence criterion which is checked at the second comparator 166 is whether the current yield ($Y_C$) is greater than or equal to the desired and specified yield (Y). In this case, the current yield ($Y_C$) may be calculated based upon the values specified at the input station 158, values derived at the processing station 158, and the current total procedure time ($t_{P-C}$) for comparison with the desired and specified yield (Y) (in some cases, this current yield calculation ($Y_C$) may have been performed in the first loop 156 and need not be repeated in the second loop 160). If the yield convergence criterion is met, the model 152 exits the second loop 160 and actually exits all the way through to the exit 151, as will be discussed below. In this case, the specified/derived values are "optimal" and the collection procedure could be performed on the device 18 using the noted values for the various control parameters.

In the event that the yield-based criterion is not met at second comparator 166, the second comparator 166 looks to a total procedure time-based convergence criterion which may be similar to that discussed above with regard to the inlet flow-based criterion (e.g., using a binary search technique with the convergence criterion then being a predetermined difference between the two most current values of the total procedure time ($t_{P-C}$)). On the first time through the second loop 160 after the noted yield-based convergence criterion has failed and the total procedure time convergence criterion has failed, the current total procedure time ($t_{P-C}$) is adjusted and the model 152 returns to the first loop 156. That is, each time that the current total procedure time ($t_{P-C}$) is adjusted in the second loop 160, the entirety of the first loop 152 is repeated (i.e., a new inlet flow ($Q_{IN}$) associated with the specified AC infusion rate ($I_{SPEC}$) is derived using the current total procedure time ($t_{P-C}$) provided by the adjustment in the second loop 160). Other convergence criterion/criteria could be used in the second loop 160, such as specifying a maximum number of iterations to be performed by the second loop 160.

In the event that the yield-based convergence criterion is not met on the second loop 160 and the total procedure time-based convergence criterion is met at the second comparator 166 in the second loop 160, the optimizer model 152 exits the second loop 160 and enters the third loop 164. The third loop 164 is an iterative adjustment of the AC ratio (R). However, the model 152 initially enters the third comparator 169 where convergence criteria (i.e., more than one) are checked. One convergence criterion is again the above-noted yield-based convergence criterion. If this yield-based convergence criterion is again not met, an AC ratio-based convergence criterion is checked at the third comparator 169. This may be similar to the inlet flow-based criterion discussed above (e.g., using a binary search technique with the convergence criterion being the two most current values of the AC ratio). On the first time through the third loop 164 after the yield-based criterion has failed and the AC ratio-based convergence criterion has failed, the AC ratio is adjusted and the optimizer model 152 returns to the first loop 152. That is, each time that the AC ratio (R) is adjusted in the third loop 164, the entirety of the first and second loops 156, 160, respectively, is repeated. Other convergence criterion/criteria could be used in the third loop 164, such as specifying a maximum number of iterations of the third loop 164.

In the event that the yield-based convergence criterion is not met in the second or third loops 160, 164, respectively, and the second and third comparator 166, 169, respectively, and the AC ratio-based convergence criterion is met at the third comparator 169 in the third loop 164, the optimizer model 152 exits the third loop 164 and enters the fourth loop 168. The fourth loop 168 is an iterative adjustment of the specified AC infusion rate ($I_{SPEC}$). However, the optimizer model 152 initially enters the fourth comparator 170 where convergence criteria (i.e., more than one) are checked. One convergence criterion is the noted yield-based convergence criterion. If the noted yield-based convergence criterion is not met at the fourth comparator 170, an AC infusion rate-based criterion is checked at the fourth comparator 170. This may be similar to the inlet-flow based criterion discussed above (e.g., using a binary search technique with the convergence criterion being the two most current values of the AC infusion rate). On the first time through the fourth loop 168 after the yield-based criterion has failed and the AC infusion rate-based convergence criterion has failed, the AC infusion rate is adjusted and the model 152 returns to the first loop 152. That is, each time that the specified AC infusion rate ($I_{SPEC}$) is adjusted, the entirety of the first, second and third loops 156, 160, 164, respectively, is repeated (with the AC ratio set back to its initial value as entered at the input station 154 on each iteration of the fourth loop 168). Other convergence criterion/criteria could be used in the fourth loop 168, such as specifying a maximum number of iterations of the fourth loop 168. In cases where the specified AC infusion rate ($I_{SPEC}$) is actually the maximum AC infusion rate, typically the fourth loop 168 will execute only a single time with a one-time increase in the AC infusion rate of, for instance, 20% (e.g., may be site-configured).

In the foregoing loops where a yield-based convergence criteria are identified, when the criteria are met the optimizer model 152 exits to exit 151 and the specified/derived (i.e., current) values for the various process control parameters may be provided to the device 18 for performing the collection procedure. However, there may be cases where no optimization occurs, such as when the optimizer model 152 exits to the exit 151 based upon the AC infusion rate based convergence criterion being met.

The optimizer model 152 may also be used for a time optimization. That is, the optimizer model will derive optimal process parameters for a predetermined total procedure time ($t_P$) through maximization of at least one of the process parameters in order to maximize the platelet collection (or for other blood component types). In this case, the optimizer model 152 only executes the first loop 156 to derive the inlet flow ($Q_{IN}$) associated with a specified AC infusion rate ($I_{SPEC}$) (typically a maximum value) using the input total procedure time ($t_P$) in this iterative derivation instead of the assumed total procedure time ($t_P$) referenced above. Once there is acceptable convergence as defined above in the product-based optimization such that model 152 exits the first loop 156, the current yield ($Y_C$) may be calculated in the first loop 156 (but again may already have been calculated in the first loop 156 at the processing station 158 such that no further calculation is required) and the convergence criterion will be met at the first comparator 162 when entering the second loop 160 (i.e., in a time-based optimization when a total procedure time is specified at the input station 154, the model 152 will exit when entering the second loop 158). As a result, the inlet flow ($Q_{IN}$) and AC infusion rate (I) will be optimal and the collection procedure may be performed with such values.

Figure 8:
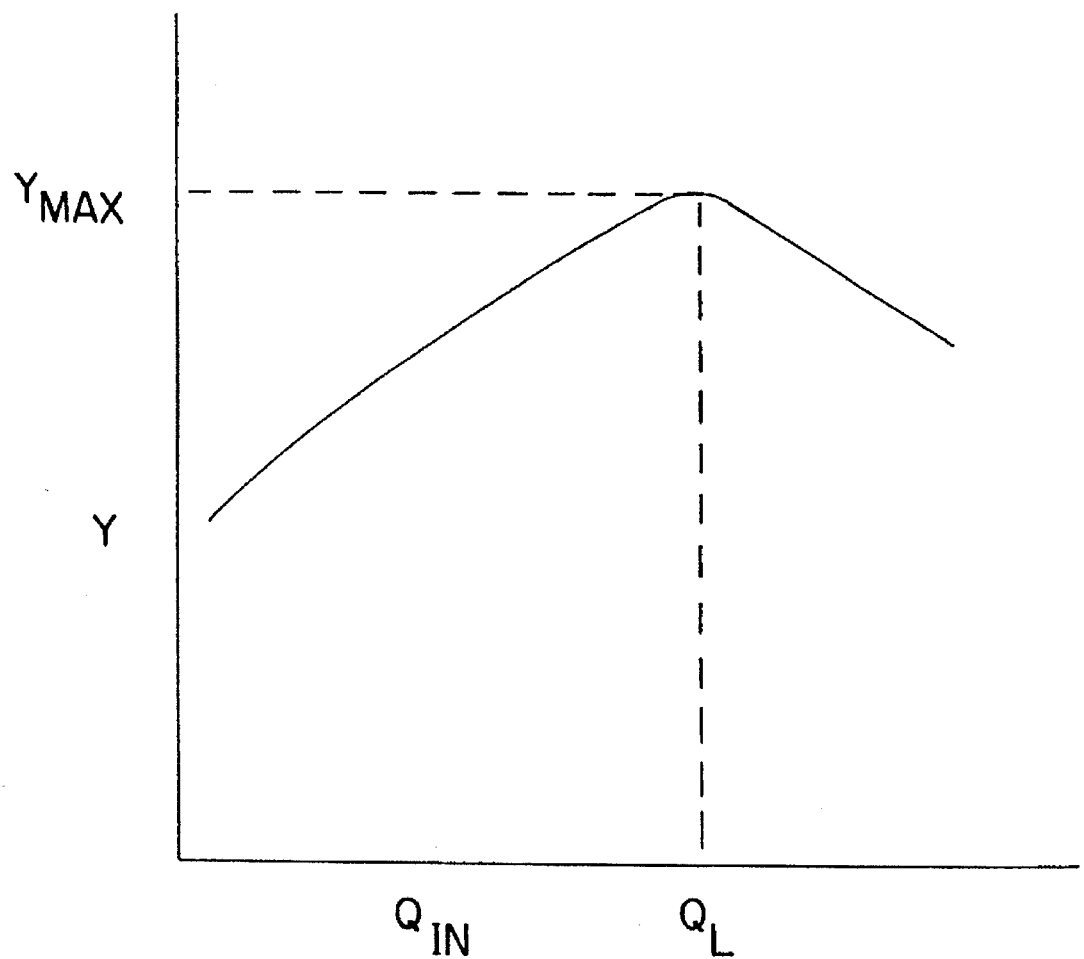
FIG. 8 is a yield/inlet flow curve.

Another optimization model is presented in FIG. 7 and may be used for both product-based and time-based optimizations. As in the case of the optimizer model 152, the optimizer model 172 may interface with the prediction model 20 or actually integrally incorporate the prediction model 20, and thus reference to Eqs. 1–22 will be further made herein. Generally, the optimizer model 172 is based upon the principle that optimization occurs when an optimal inlet flow ($Q_L$) associated with an optimum system collection efficiency is used in the derivation of various process control parameters. Referring to FIG. 8, a representative inlet flow ($Q_{IN}$)/yield (Y) curve is presented to show the optimal inlet flow ($Q_L$) associated with the maximum yield ($Y_{MAX}$). This optimal inlet flow ($Q_L$) is mathematically expressed by Eq. 23 presented below which results from differentiating Eq. 4 of the prediction model 20 with regard to the inlet flow ($Q_{IN}$). As can be appreciated, where different algorithms are used in the associated prediction model (whether based upon collection of blood components other than platelets, different collection apparatus, or alternative derivations of the various parameters with the same collection procedure and apparatus), the optimal inlet flow may be mathematically expressed in a different manner.

$$Q_L = \left( \frac{C_1}{2C_2} \right) e^{-9.91(1-1/R)H} - C_3 \tag{Eq. 23}$$

$$C_3 = \frac{1}{2(t_P/K_7 - 1/K_9)}, \quad Q_0 \geq \begin{array}{l} 45 \text{ for Dual Needle ("DN")} \\ 20 \text{ for Single Needle ("SN")} \end{array} \tag{Eq. 24}$$

$$= 0, \quad \begin{array}{l} Q_0 < 45 \text{ for } DN \\ < 20 \text{ for } SN \end{array} \tag{Eq. 25}$$

$$K_7 = 500 \, (DN) \quad K_9 = 45 \, (DN) \tag{Eq. 26}$$
$$= 215 \, (SN) \quad = 20 \, (SN)$$

$$C_1 = 0.803 \, (SN, DN \text{ without stepdown}) \tag{Eq. 27}$$
$$= 0.840 \, (DN \text{ with stepdown})$$

$$C_2 = 4.08 \times 10^{-5} \, (DN) \tag{Eq. 28}$$
$$= 8.54 \times 10^{-5} \, (SN)$$

Based upon the foregoing, the optimal inlet flow ($Q_L$) is really "optimal" in terms of the collection apparatus.

Referring again to FIG. 7, the optimizer model 172 will initially be described with regard to a product-based optimization wherein the desired yield (Y) is specified at input station 184. Generally, the inlet flow ($Q_{IN}$) associated with a specified AC infusion rate ($I_{SPEC}$) (typically the maximum AC infusion rate and also specified at input station 184) is iteratively derived from certain other specified parameters. This inlet flow calculation, particularly when the maximum AC infusion rate ($I_{MAX}$) and maximum AC ratio ($R_{MAX}$) are specified, the inlet flow ($Q_{IN}$) is optimal based on the physiological considerations of the donor 14. This is primarily through the solution of Eqs. 4, 8, 14, and 16 and/or equations ancillary thereto by the prediction model 20 discussed above. For purposes of solving these equations certain parameters remain fixed in the iterative derivation of the inlet flow ($Q_{IN}$) which achieves the specified AC infusion rate ($I_{SPEC}$) and these parameters are also specified at input station 184. These include the total blood volume ($V_B$) which can be calculated using Eq. 10 since the donor's height, weight, and sex are entered in the central input station 148, and the AC ratio (R), which can be calculated using Eq. 9 since the donor's hematocrit (H) has been determined, or may be specified at some maximum value. Moreover, the total procedure time ($t_P$) remains fixed in each iterative derivation of the inlet flow ($Q_{IN}$) associated with the specified AC infusion rate ($I_{SPEC}$). However, since the total procedure time (tP) is not known in the case of a product-based optimization and thus cannot be specified at the input station 184, a current total procedure time ($t_{P-C}$) initially will be assumed (e.g., this assumption is configured in the optimizer model 172 and since a range of total procedure times is provided in the prediction model 20 as noted above, the mean total procedure time ($t_P$) is typically configured into this portion of the optimizer model 172 as the initial current total procedure time ($t_{P-C}$)). The "current" designation is used for the total procedure time in this case since the optimizer model 172 provides for an adjustment of the total procedure time after each iterative determination of the inlet flow ($Q_{IN}$) which provides the specified AC infusion rate ($I_{SPEC}$) in order to achieve the desired yield (Y) if required in the case of a product-based optimization as will be discussed in more detail below.

The solution of Eqs. 4, 8, 14, and 16 also requires that certain values initially be assumed for certain of the remaining parameters. In this case, an iterative procedure is used in the solution of the yield equation (Eq. 4) (and including equations ancillary thereto as noted above) and updated values are used in the next iterative calculation(s) at the processing station 188. Although the derivation of that inlet flow ($Q_{IN}$) which provides the specified (typically maximum) AC infusion rate ($I_{SPEC}$) may be accomplished in a variety of manners via Eqs. 4, 8, 14, and 16, one way is to assume a current value for the plasma collect factor (P), then calculate the current inlet flow ($Q_{IN-C}$) using the specified AC infusion rate ($I_{SPEC}$), then calculate the current yield ($Y_C$), then calculate the current plasma collection factor ($P_C$) using the current yield ($Y_C$), and repeat the foregoing with the updated parameters, all within the processing station 188, until there has been acceptable convergence on the current inlet flow ($Q_{IN-C}$) in relation to the specified AC infusion rate ($I_{SPEC}$).

In addition to the calculation of the current inlet flow ($Q_{IN-C}$) associated with the specified AC infusion rate ($I_{SPEC}$), the above-discussed optimal inlet flow ($Q_L$) is calculated at processing station 192. Consequently, a comparison can be made between the current inlet flow ($Q_{IN-C}$) which was derived in the above-described manner and the optimal inlet flow ($Q_L$) at the first comparator 176. If the current inlet flow ($Q_{IN-C}$) is less than the optimal inlet flow ($Q_L$) at the first comparator 176, the specified values for the various parameters associated with the inlet flow $Q_{IN}$ are "optimum", namely the AC ratio (R) and the AC infusion rate (I) specified at the input station 184. Thereafter, the current yield ($Y_C$) (which was calculated in the derivation of the current inlet flow ($Q_{IN-C}$) associated with the specified AC infusion rate ($I_{SPEC}$) at the processing station 188) is compared with the input yield (Y) at second comparator 180. In the event that there has been acceptable convergence between these yield values, the current total procedure time ($t_{P-C}$) is also "optimal". However, in the event that there has not been acceptable convergence between these yield values, the current total procedure time ($t_{P-C}$) is adjusted at adjusting station 196 and the foregoing iterative derivation of the current inlet flow ($Q_{IN-C}$) associated with the specified AC infusion rate ($I_{SPEC}$) is repeated until such convergence is achieved (i.e., using the initially specified AC infusion rate ($I_{SPEC}$) and the now adjusted current total procedure time ($t_{P-C}$), a new current inlet flow ($Q_{IN-C}$) is iteratively derived in the above-described manner).

Referring back to the first comparator 176, if the current inlet flow ($Q_{In-C}$) associated with the specified AC infusion rate ($I_{SPEC}$) derived at processing station 188 is greater than the optimal inlet flow ($Q_L$), a current AC infusion rate ($I_C$) associated with this particular inlet flow ($Q_L$) is iteratively derived at the processing station 188 generally in the above-described manner (i.e., the initially specified AC infusion rate ($I_{SPEC}$) is disregarded in this derivation and a current AC infusion rate ($I_C$) is iteratively derived to coincide with the inlet flow ($Q_L$)). In this case, the current inlet flow ($Q_{IN-C}$) will always be equal to the optimal inlet flow ($Q_L$) at the first comparator 176 and the optimizer model 172 thereafter proceeds to the second comparator 180 for the yield comparison in accordance with the above-described procedure.

The optimizer model 176 may also be used for a time-based optimization. In this case, the total procedure time ($t_P$) is specified at the input station 184 as a specified total procedure time ($t_{P-SPEC}$) and thus is not assumed as in the product-based optimization. The optimizer model 172 thereafter proceeds in the same manner discussed above with regard to the product-based optimization except at the second comparator 180. Since no yield was input there is no yield comparison made at the second comparator 180. Instead a total procedure time comparison is made at the second comparator 180. Since the current total procedure time ($t_{P-C}$) was set equal to the specified total procedure time ($t_{P-SPEC}$) prior to the model 172 proceeding to the processing station 188 in this time-based optimization, the model 172 will exit each time at the second comparator for a time-based optimization. In addition to the above-described product-based and time-based optimizations, principles of the present invention may be extended to other applications relating to enhancing blood component system management. For instance, an optimization in accordance with principles of the present invention may be extended to encompass donor management issues. In one such case, another "optimization" associated with the blood component collection process would be to collect blood components as dictated by existing inventory (i.e., use optimization as an inventory control mechanism). That is, information relating to the inventory of the various types of blood components in the blood bank/center and/or the demand for one or more blood component types could be maintained such that specific collection procedures could be selected to accommodate for a low supply of a given blood component type and/or a high demand for such blood component type. More specifically, in the event that the supply of red blood cells was low and/or the demand for red blood cells was high, or anticipated to be so in the near future, prompts could be provided to operators that red blood cells should be selected for collection if possible from donors during a given time period. Relatedly, the optimization principles of the present invention would be applicable to maintaining data on blood component collections from a given donor such that a determination could be made as to what type or types of blood components from the particular donor provided the maximum yield in the collection procedure. That is, information could be collected and maintained from prior blood component donations such that a determination could be made for a specific donor as to which type or types of blood components the donor has had a propensity to produce maximum yields therefor.

Notwithstanding the foregoing description of the present invention in relation to an on-line blood component collection process, those skilled in the art will appreciate that the source of blood may be provided to the blood component collection device from an appropriate blood container (not shown) interconnected with the blood component collection device 18 versus receiving such directly from the donor. Moreover, the blood of course may be provided from alternative sources such as animals. Furthermore, as illustrated in FIG. 3 the described platelet harvesting procedure may be performed utilizing a single needle configuration. In addition, the present invention is applicable to the collection of other types of blood components such as red blood cells, white blood cells, and/or plasma, and is further applicable to the simultaneous collection of more than one blood component type. In the case of red blood cell collection and optimization in accordance with principles of the present invention, the donor's blood type should be known and used in various algorithms. Moreover, the present invention is not limited to the source being whole blood. That is, the principles of the present invention may be applicable to removal of a component from any liquid.

The above-identified type of optimizations for a blood component collection facility such as a blood bank/center are based upon maintaining one or more appropriate data bases of information relating to blood component collection procedures and providing a basis for evaluating this data through display/report generation capabilities. As noted above, some of this data may be information which is manually entered into an appropriate data base at the central input station 148 and/or at any one of the various operator interface modules 16, as well as data which is collected and recorded during performance of a given blood component collection procedure. Moreover, at least some of this data is used to control the collection procedure being performed with the blood component collection device 18. As such, a first station or the central input station 148, at least one second station or the interface modules 16, and the information communication medium therebetween (e.g., via manual transfers of one or more computer disks 142 or electronic transfers via an appropriate network system as noted above) may also be categorized as a blood component collection control and information communication system.

The blood component collection control and communication system may be utilized as follows and generally corresponds with the discussion above on a process parameter optimization basis. However, other optimizations of the system 2 using the noted blood component collection control and communication system do not require that process parameter optimization necessarily be used. Nonetheless, and with regard to the system 2 described above, a donor will typically come to the blood bank/center and check in with an operator at the central input station 148. Various types of biological data on the donor and physical and medical characteristics of the donor, such as those observed and recorded during prior "procedures" performed on the donor, may be edited (in the case of a donor already in the data base) or entered (new donors) at the central input station 148 (via its information input device or keyboard in the case of the station 148 being a PC). The central input station 148 which interacts with the one or more data bases and displays various information to the operator at the station 148 (e.g., via its monitor in the case of the station 148 including a PC). Moreover, various data relating to the process parameters for controlling the blood component collection device 18 may also be entered and/or edited and/or displayed at the central input station 148. As noted above, this type of information is used to generate an initial procedure order (which as noted includes the generation or derivation of at least one process control parameter for the collection device 18 from the noted types of data) for the donor and the specified collection procedure. Various other data may be displayed to the operator at the central input station 148 at this time, for instance regarding the donor (e.g., blood component yields achieved in prior collection procedures performed on the donor) and/or process control parameters used prior collection procedures, which may also be utilized in the generation of the initial procedure order.

Once again, the foregoing data entry and initial procedure order generation procedures could be performed at the designated operator interface module 16 (e.g., a PC as noted which thus includes a keyboard and monitor) as well. The operator interface modules 16 each directly interface with their respective blood component collection device 18, as opposed to the central input station 148 which is not so directly interfaced with the various devices 18. Nonetheless, the initial procedure order and its accompanying data is stored in the operator interface module 16 associated with the blood component collection device 18 to be used in the collection procedure for the donor.

The operator interface module 16 controls the operation of the blood component collection device 18 during the collection procedure being performed on the donor via its interface and continuously displays various data. The interface module also receives and/or records and/or displays various data during the procedure as well, such as the blood component yield of the blood component type being separated, removed, and collected from the device 18. Moreover, the interface module 16 may be used to alter the procedure order (e.g., one or more of the process control parameters) during the collection procedure under certain situations.

Once the procedure is completed, the data recorded from the procedure via the operator interface module 16 may be displayed to the operator (e.g., yield). Moreover, this data may be transferred back to the central input station 148 for display and recordation purposes in the noted data base(es). Moreover and as noted, this data may be used in the optimization of blood bank/center operators via various data compilations and the display and/or production of such into a written report format for analysis. Although it may of course be possible to perform data manipulation and/or report generation operations at an operator interface module 16, it may be more effective from an overall operations standpoint to perform such operations at other locales, such as at the central input station 148.

Although the discussion thus far on the collection procedures has been donor-specific, it will be appreciated that this same information may also be relevant to evaluating patient needs, that is individuals to which the collected blood components are administered for therapeutic treatment purposes. Consequently, certain blood banks/centers such as hospitals may also maintain patient information/data in addition to donor data and further benefit from optimization principles of the present invention. Since certain blood banks/centers are thus multifunctional in that they not only engage in blood component collection activities but blood component administration activities as well, the display/ report formats discussed below which are particularly applicable to both donors and patients are so identified.

Typically, a blood bank/center has a group of donors which with some degree of regularity undergo some type of blood component collection procedure at the blood bank/ center or a patient which regularly undergoes some type of blood component therapy. Moreover, there are of course a substantial number of donors which undergo the noted types of blood component collection procedures on a more irregular basis, as well as patients which may require blood component therapy on an irregular basis. In any case, the blood bank/center may maintain data on each of its donors and the various blood component collection procedures which they undergo for purposes of maintaining and generating certain donor-specific reports, as well as on each of its patients and the various therapeutic treatments which they undergo for maintaining patient-specific reports. For instance, data may be maintained for a file report on each donor/patient, one example of which is set forth in FIGS. 9A–G. This donor/patient-specific file report may include demographics information, blood and platelet typings information, disease and viral screenings information, contacts information, hematology information, blood chemistry information, procedures information (e.g., collection for donors, administration for patients) performed over a specified time period, therapeutics information, procedure summaries over a specified time period, and procedure machine information for procedures performed over a specified time period.

Additional reports which the blood bank/center may utilize to analyze its data on donor/patient-related information may be formulated from various groupings of the above-identified types of information for a given donor. For instance, an example of a donor/patient vitals report is presented in FIGS. 10A–B and could include blood and platelet typings information and disease and viral screenings information. Moreover, a donor/patient vitals report may include, for each visit by the given donor/patient to the blood bank/center for collection/administration procedures over a specified period of time, hematology information, blood chemistry information, and vitals information.

The blood bank/center may also maintain data relating to each blood component collection procedure for each donor as a management tool. For instance, this data may be utilized to generate a procedure summary report on a per donor/per collection procedure basis. Generally, a procedure summary report provides certain information on the type of collection procedure which was performed on the donor (e.g., platelet collection via a dual needle collection configuration), as well as the results of the collection efforts and including the yield or the number of blood components collected (e.g., the number of platelets which were collected during the procedure). An example of such a procedure summary report is presented in FIGS. 11A–B. Relatedly, this same data may be used to produce a donor product report which specifies various characteristics of the collected blood component(s) (e.g., yield), an example of which is illustrated in FIG. 12.

Another report relating to a particular collection procedure for a donor is a procedure machine report which documents the activities which occurred during the procedure, an example of which is presented in FIGS. 13A=14 B. Finally, a run data report (FIGS. 14A–D) and a donor/patient procedure report (FIGS. 15A–D) for a given collection procedure for a given donor may include the types of information presented in the procedure summary report and the procedure machine report, as well as various other information relating to the particular procedure which was performed on the donor. This type of data, particularly if evaluated over multiple procedures, may be particularly useful in "standardizing" a set of blood component collection procedure parameters for a given donor until some condition necessitates a change. That is, the maintenance of data on the collection procedure parameters for a given donor over multiple procedures may establish a "norm" for the collection procedure parameters which are appropriate for a given donor, for instance such that the process control parameters do not have to be generated on every visit by the donor to the blood bank/center. These standardized operating process control parameters would then not necessarily have to be changed absent a change in certain conditions, such as reflected by data collected during a subsequent procedure and/or a change in donor-specific data.

Another particular display/report format which may be used in the optimization of the blood bank/center operations is a procedure history report for a particular donor, an example of which is presented in FIG. 16. A procedure history report for an identified donor over a specified period of time (i.e., encompassing a time period in which a number of blood component collection procedures were performed on the donor) may include information of the type of blood component collected in each procedure and the yield associated therewith. This type of data may be utilized to generate a report on the "productivity" of the donor over a period of time. That is, the data could be used to generate a report of the type (e.g., platelet) and yield of each blood component collection procedure for a donor (i.e., the number of the particular blood component type which was collected during a particular procedure). This type of report also serve to identify certain trends, that is that a particular donor is more productive for one type of blood component than another (e.g, a more appropriate red blood cell source than platelet source). It may also be useful to generate this types of procedure history reports on a multiple donor basis.

The data which is maintained by the blood bank/center on each collection procedure for each donor may also be used to generate reports which further assist the blood bank/center in managing its overall business activities. For instance, this data may be used to generate a production report for the blood bank/center which is generally directed to overall production-like statistics (e.g., the total number of all collection procedures which were performed over a given time period, as well as the total number of each particular type of collection procedures which were performed over a given time period). An example of a production report is presented in FIGS. 17A–C. Moreover, the data maintained by the blood bank/center may also be used to generate a staff report which is generally directed to how many collection procedures a given operator has been responsible for over a specified time period. An example of a staff report is presented in FIG. 18. Furthermore, the data maintained by the blood bank/center may be used to generate a statistics report which summarizes the types of and numbers of collection procedures which were performed over a given time period, and thereby reflects the usage of the blood bank/center over a given period of time. An example of a statistics report is presented in FIG. 19. In addition, the data maintained by the blood bank/center as noted may be utilized for inventory control. That is, the blood bank/center may maintain data on the number of each of the type of blood component product which it has in inventory and the demand for each type of blood component product, or more specifically the number and type of blood component products which are disbursed or distributed by the blood bank/center over a given time period.

As noted, optimization principles of the present invention may also be applied to management issues in relation to donor availability and patient needs. For instance, data maintained by the blood bank/center may be used to generate lists of donors and patients, a representative example of which is illustrated in FIGS. 20A–B. Moreover, donor search reports may be generated to provide listing of donors meeting certain criterion, an example of which is presented in FIGS. 21A–C.

Although not necessarily required, the format of data entry may actually emulate the format of the data in which it is displayed at the central input station 148 and/or at an operator interface module 16, as well as the format of such data in hard copy form (e.g., a written report) discussed above. As such, the above discussion on report formats and contents, may be applicable/utilized for data entry purposes and/or display purposes as well.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention, and such other embodiments, and with various modifications required by the particular applications or uses of the present invention. It is intended that the appended claims be construed to include alternative embodiments to the extent permitted by the prior art.

What is claimed is:

1. A blood component collection control and information communication system used in conjunction with a blood component collection device in a procedure performed on a donor to separate, remove and collect components from blood received from the donor, comprising:

an information communication medium;

a first station interactive with the communication medium to transmit and receive information on the medium describing biological data of the donor, describing process parameters for controlling the collection device during the procedure performed on the donor, describing physical and medical characteristics of the donor observed during performance of a prior procedure on the donor, and describing the yield of at least one component obtained from the donor during performance of the procedure; the first station including an information input device by which to supply donor data, process parameters, prior procedure characteristics and component yield information to communication medium; the first station further including a computer responsive to the donor data, prior procedure characteristics and component yield information received from the communication medium to determine at least one process parameter to be used for controlling the blood component collection device during performance of a subsequent procedure on the donor; and the first station also including a display by which to display the donor data, process parameters, prior procedure characteristics and component yield information;

a second station interactive with the communication medium to transmit and receive information on the medium describing biological data of the donor, describing process parameters for controlling the collection device during the procedure performed on the donor, describing physical and medical characteristics of the donor observed during performance of a prior procedure on the donor, and describing the yield of at least one component obtained from the donor during performance of a procedure; the second station including an information input device by which to supply donor data, process parameters, prior procedure characteristics and component yield information to communication medium; the second station further including a computer responsive to the donor data, prior procedure characteristics and component yield information received from the communication medium to determine at least one process parameter to be used for controlling the blood component collection device during performance of a subsequent procedure on the donor; and the second station also including a display by which to display the donor data, process parameters, prior procedure characteristics and component yield information; and an interface of at least one of the first or second stations which connects to the blood component collection device to the one station, the interface adaptable for controlling the blood collection device to perform the procedure in response to the process parameter information transmitted to the one station by the communication medium; the interface further supplying information to the medium at the one station describing the yield of at least one component obtained from the donor during performance of the procedure performed.

2. A blood component collection control and information communication system as defined in claim 1 wherein:

the second station is connected through the interface to the blood component collection device and the first station is not connected to a blood component collection device; and the computer of the first station is further operative to generate donor report information describing the procedure performed on each donor and the yield information of each donor from the information received from the medium from the second station, and the display of the first station is operative to display the information.

3. A blood component collection control and information communication system as defined in claim 2 wherein:

the computer of the first station is further operative to generate management report information based on the collective information from a plurality of donor reports.

4. A blood component collection control and information communication system as defined in claim 3 further comprising:

a plurality of second stations which are all interactive with a single first station by the communication medium.

5. A blood component collection control and information communication system as defined in claim 4 wherein:

the components include one of platelets, blood cells and plasma.

6. A blood component collection control and information communication system as defined in claim 5 wherein:

the management report information includes information describing the net inventory of the quantity of one of the platelets, blood cells or plasma based on the quantity of one of the platelets, blood cells or plasma collected and dispensed over a predetermined time period.

7. A blood component collection control and information communication system as defined in claim 5 wherein:

the management report information includes information describing the quantity of one of the platelets, blood cells or plasma collected from each donor over a predetermined time period.

8. A blood component collection control and information communication system as defined in claim 5 wherein:

the management report information includes information describing the procedures performed over a predetermined period of time.

9. A blood component collection control and information communication system as defined in claim 5 wherein:
the computer of the first station records the information associated with each procedure performed on each donor; and
the management report information is derived from the information recorded by the computer of the first station.

10. A blood component collection control and information communication system as defined in claim 1 wherein:
the computer of the one station further calculates predicted component yield information from the donor data, process parameters, prior procedure characteristics information.

11. A blood component collection control and information communication system as defined in claim 1 wherein:
the process parameter information is standardized for each separate donor according to the biological data information of each donor and until prior procedure characteristic information requires modification of the standardized process parameter information.

12. A blood component collection control and information communication system as defined in claim 1 wherein the communication medium comprises a removable computer disk.

13. A blood component collection control and information communication system as defined in claim 1 wherein the communication medium comprises an electronic network interconnecting the first and second stations.

14. A method of controlling a blood component collection device in a procedure performed on a donor to separate, remove and collect components from blood received from the donor and for communicating information describing the procedure, comprising the steps of:
establishing first and second stations, each of which includes a computer, an information input device and a display;
connecting one of the first and second stations to the blood component collection device;
communicating information between the first and second stations which describes biological data of the donor, process parameters for controlling the collection device during the procedure performed on the donor, physical and medical characteristics of the donor observed during performance of a prior procedure on the donor, and the yield of at least one component obtained from the donor during performance of the procedure;
using the information input device at either the first or the second station to create at least some of one of the donor data information, the process parameter information, the prior procedure characteristics information and the component yield information;
deriving at least some of the process parameter information by processing the donor data, prior procedure characteristics and component yield information with the computer at one of the first or second stations; and
controlling the operation of the blood component collection device in response to the process parameter information which was communicated, created by using the information input device and derived from the computer.

15. A method as defined in claim 14 further comprising the step of:
deriving at least some of the yield information by processing with the computer at the one station following performance of the procedure performed.

16. A method as defined in claim 15 further comprising the step of:
predicting component yield information from the donor data, process parameters, prior procedure characteristics information by processing with the computer at one of the first or second stations prior to performance of the procedure performed.

17. A method as defined in claim 14 further comprising the step of:
displaying at least some of the donor data, process parameters, prior procedure characteristics and component yield information at the display of one of the first and second stations.

18. A method as defined in claim 14 further comprising the step of:
generating donor report information describing the procedure performed on each donor and the yield information of each donor from the information communicated from the second station by processing with the computer of the first station.

19. A method as defined in claim 18 further comprising the step of:
generating management report information by processing with the computer of the first station the collective information from a plurality of donor reports.

20. A method as defined in claim 19 further comprising the step of:
communicating the information between the first station and a plurality of second stations.

21. A method as defined in claim 20 wherein the components include one of platelets, blood cells and plasma.

22. A method as defined in claim 21 further comprising the step of:
including information in the management report which describes the net inventory of the quantity of one of the platelets, blood cells or plasma based on the quantity of one of the platelets, blood cells or plasma collected and dispensed over a predetermined time period.

23. A method as defined in claim 22 further comprising the step of:
including information in the management report which describes the quantity of one of the platelets, blood cells or plasma collected from each donor over a predetermined time period.

24. A method as defined in claim 22 further comprising the step of:
including information in the management report which describes the procedures performed over a predetermined period of time.

25. A method as defined in claim 22 further comprising the steps of:
recording the information associated with each procedure performed on each donor in the computer of the first station; and
deriving the management report information from the information recorded by the computer of the first station.

26. A method as defined in claim 14 further comprising the step of:

standardizing the process parameter information for each separate donor according to the biological data information of each donor; and thereafter modifying the standardized process parameter information by processing with the computer of one of the first or second stations based on the prior procedure characteristic information.

27. A method as defined in claim 14 wherein the step of communicating the information further comprises:

transporting a removable computer disk containing the information between the first and second stations.

28. A method as defined in claim 14 wherein the step of communicating the information further comprises:

transmitting and receiving the information between the first and second stations electronically over a network.

* * * * *